(12) United States Patent
Maloney et al.

(10) Patent No.: US 10,768,154 B2
(45) Date of Patent: Sep. 8, 2020

(54) RATIOMETRIC QUANTUM DOT-RHODAMINE B SENSING COMPOUND AND DEVICE MADE FROM THE COMPOUND

(71) Applicant: Colgate-Palmolive Company, New York, NY (US)

(72) Inventors: Venda Porter Maloney, Piscataway, NJ (US); Donghui Wu, Bridgewater, NJ (US); Long Pan, Somerset, NJ (US); Preston Snee, Chicago, IL (US); Armen Shamirian, Chicago, IL (US)

(73) Assignee: Colgate-Palmolive Company, New York, NY (US)

( * ) Notice: Subject to any disclaimer, the term of this patent is extended or adjusted under 35 U.S.C. 154(b) by 489 days.

(21) Appl. No.: 15/464,643

(22) Filed: Mar. 21, 2017

(65) Prior Publication Data

US 2017/0269046 A1    Sep. 21, 2017

Related U.S. Application Data

(60) Provisional application No. 62/311,148, filed on Mar. 21, 2016.

(51) Int. Cl.
| | | |
|---|---|---|
| *G01N 33/00* | (2006.01) | |
| *C09K 11/88* | (2006.01) | |
| *C09K 11/02* | (2006.01) | |
| *C09K 11/06* | (2006.01) | |
| *C09B 11/24* | (2006.01) | |
| *G01N 33/84* | (2006.01) | |

(52) U.S. Cl.
CPC .......... *G01N 33/0044* (2013.01); *C09B 11/24* (2013.01); *C09K 11/02* (2013.01); *C09K 11/06* (2013.01); *C09K 11/883* (2013.01); *G01N 33/84* (2013.01)

(58) Field of Classification Search
CPC ...................................................... G01N 33/00
USPC ............................................................ 436/120
See application file for complete search history.

(56) References Cited

U.S. PATENT DOCUMENTS

| | | |
|---|---|---|
| 9,155,497 B1 | 10/2015 | Plumley et al. |
| 2010/0311903 A1 | 12/2010 | Rajagopalan |
| 2012/0282632 A1 | 11/2012 | Chiu et al. |
| 2013/0260014 A1 | 10/2013 | Clark et al. |
| 2014/0200333 A1 | 7/2014 | Terpetschnig et al. |

FOREIGN PATENT DOCUMENTS

| | | |
|---|---|---|
| EP | 2217281 | 8/2010 |
| EP | 2457509 | 5/2012 |
| KR | 2016 0095387 | 8/2016 |

(Continued)

OTHER PUBLICATIONS

Shi, L. et al, Journal of the American Chemical Society 2006, 128, 10378-10379.*

(Continued)

*Primary Examiner* — Arlen Soderquist

(57) ABSTRACT

The present disclosure is directed to a sensing agent. The sensing agent comprises a quantum dot; and a dye moiety coupled to the quantum dot. The sensing agent is capable of sensing at least one analyte chosen from hydrogen sulfide ($H_2S$) and bisulfide. Sensors made from the sensing agents are also disclosed.

8 Claims, 9 Drawing Sheets

(56) References Cited

FOREIGN PATENT DOCUMENTS

| WO | WO 2009/061473 | 5/2009 |
|---|---|---|
| WO | WO 2011/133595 | 10/2011 |

OTHER PUBLICATIONS

Snee, P. T, et al, Journal of the American Chemical Society 2006, 128, 13320-13321.*
Shi, L. et al, Analytical Chemistry 2007, 79, 208-214.*
Wang, L. et al, Chemistry Letters 2008, 37, 402-403.*
Suzuki, M. et al, Journal of the American Chemical Society 2008, 130, 5720-5725.*
Crivat, G. et al, Journal of the American Chemical Society 2010, 132, 1460-1461.*
Sarkar, S. et al, Journal of Physical Chemistry Letters 2010, 1, 636-640.*
Page, L. E. et al, Chemical Communications 2011, 47, 7773-7775.*
Grimm, J. B. et al, Organic Letters 2011, 13, 6354-6357.*
Xu, Z. et al, Chemical Communications 2012, 48, 10871-10873.*
Peng, B. et al, Chemistry—A European Journal 2014, 20, 1010-1016.*
Tyrakowski, C. M. et al, Analytical Chemistry 2014, 86, 2380-2386.*
Wei, L. et al, Scientific Reports 2014, 4, paper 4521, 6 pages.*
Du, F. et al, Small 2014, 10, No. 5, 964-972.*
Gu, X. et al, RSC Advances 2014, 4, 50097-50101.*
Yuan, L. et al, Chemical Science 2015, 6, 2360-2365.*
Adamczyk, . et al, Bioorganic & Medicinal Chemistry Letters 2003, 13, 2327-2330.*
Pullela, P. K. et al, Analytical Biochemistry 2006, 352, 265-273.*
Sun H. et al, Chemistry of Materials 2006, 18, 3381-3384.*
Xu, L. et al, Journal of Physical Chemistry C 2011, 115, 16315-16321.*
Li, X. et al, Chinese Science Bulletin 2015, 58, 2657-2662.*
Huang, K. et al, Dyes and Pigments 2015, 118, 88-94.*
Funston, A. M. et al, Advanced Materials 2008, 20, 4274-4280.*
Boulesbaa, A. et al, Journal of Physical Chemistry C 2010, 114, 962-969.*
Brunet, A. et al, Bioorganic & Medicinal Chemistry Letters 2014, 24, 3186-3188.*
Almy, 1925, "A Method for the Estimation of Hydrogen Sulfide in Proteinaceous Food Products," J. American Chemical Society 47:1381-1390.
Ast et al., 2014, "pH-responsive quantum dots (RQDs) that combine a fluorescent nanoparticle with a pH-sensitive dye," Physical Chemistry Chemical Physics 16(46):25255-25257.
Chen et al., 2012, "Reaction-Based Genetically Encoded Fluorescent Hydrogen Sulfide Sensors," J. American Chemical Society 134:9589-9592.
Chen et al., 2013, "A Ratiortetric Fluorescent Probe for Rapid Detection of HydrogenSulfide in Mitochondria," Angew. Chem. Int. Ed. Engl. 52:1688-1691.
Choi et al., 2009, "Sulfide-Selective Chemosignalina by a Cu2+ Complex of Dipicolylamine Appended Fluorescein," Chemical Communications (Camb.) (47):7390-7392.
Doeller et al., 2005, "Polarographic Measurement of Hydrogen Sulfide Production and Consumption by Mammalian Tissues," Analytical Biochemistry 341:40-51.
Feng et al., 2016, "A new ratiometric fluorescent probe for rapid, sensitive and selective detection of endogenous hydrogen sulfide in mitochondria," Chemical Communications—ChemCOM 52(15):3131-3134.
Furne et al., 2008 "Whole Tissue Hydrogen Sulfide Concentrations Are Orders of Magnitude Lower Than Presently Accepted Values," Am. J. Physiol. Regul. Integr. Comp. Physiol. 295:R1479-1485.
Giuliani et al., 2013, "Hydrogen Sulfide Slows Down Progression of Experimental Alzheimer's Disease by Targeting Multiple Pathophysiological Mechanisms," Neurobiology of Learning and Memory 104:82-91.

Goldman et al., 2005. "A Hybrid Quantum Dot-Antibody Fragment Fluorescence Resonance Energy Transfer-Based TNT Sensor," J. American Chemical Society 127:6744-6751.
Goodwin et al., 1989, "Determination of Sulfide in Brain Tissue by Gas Dialysis/Ion Chromatography: Postmortem Studies and Two Case Reports," J. Analytical Toxicology 13:105-109.
Gui et al., 2012, "Rhodamine 6G conjugated-quantum dots used for highly sensitive and selective ratiomctric fluorescence sensor of glutathione," Talanta 94:295-300.
Guo et al., 2015, "Fluorescence Chemosensors Hydrogen Sulfide Detection Biological Systems," The Analyst 140:1772-1786.
Han et al., 2006, "Hydrogen Sulfide and Carbon Monoxide Are in Synergy with Each Other in the Pathogenesis of Recurrent Febrile Seizures." Cellular Molecular Neurobiology 26(1):101-107.
Hyspler et al., 2002, "A Simple, Optimized Method for the Determination of Sulphide in Whole Blood by Ge-Ms as a Marker of Bowel Fermentation Processes," J. Chromatography B 770:255-259.
International Search Report and Written Opinion of the International Searching Authority in International Application No. PCT/US2017/023319, dated Jun. 6, 2017.
Kabil et al., 2010, "Redox Biochemistry of Hydrogen Sulfide," J. Biol. Chem. 285(29):21903-21907.
Kartha et al., 2012, "Enhanced Detection of Hydrogen Sulfide Generated in Cell Culture Using an Agar Trap Method," Analytical Biochemistry 423:102-108.
Lei et al., 1989, "Determination of Sulfide and Mercaptans in Caustic Scrubbing Liquor," Analytica Chimica Acta 226(1):165-170.
Lippert et al., 2011, "Reaction-Based Fluorescent Probes for Selective Imaging of Hydrogen Sulfide in Living Cells," J. American Chemical Society 133:10078-10080.
Liu et al., 2011, "Capture and Visualization of Hydrogen Sulfide by a Fluorescent Probe." Angew. Chem. Int. Ed. Engl. 50:10327-10329.
Lou et al., 2010, "Displacement Method to Develop Highly Sensitive and Selective Dual Chemosensor Towards Sulfide Anion," The Analyst 136(4):684-687.
Medintz et al., 2003, "Self-Assembled Nanoscale Biosensors Based on Quantum Dot FRET Donors," Nature Materials 2:630-638.
Mitchell et al., 1993, "High-Performance Liquid Chromatography Detection of Sulfide in Tissues from Sulfide-Treated Mice," J. Applied Toxicology 13(6):389-394.
Montoya et al., 2012, "Selective Turn-on Fluorescent Probes for Imaging Hydrogen Sulfide in Living Cells," Chem. Communications (Camb.) 48:4767-4769.
Nagata et al., 199 "Sulfide Concentrations in Postmortem Mammalian Tissues," J. Forensic Science 35:706-712.
Nagy et al., 2014, "Amperometric Cell for Subcutaneous Detection of Hydrogen Sulfide in Anesthetized Experimental Animals," Physiological Measurement 35:2475-2487.
Ogasawara et al., 1993, "Determination of Bound Sulfur in Serum by Gas Dialysis/High-Performance Liquid Chromatography," Analytical Biochemistry 215:73-81.
Olson et al., 2009, "Is Hydrogen Sulfide a Circulating "Gasotransmitter" in Vertebrate Blood?" Biochimica Biophysica Acta 1787:856-863.
Peng et al., 2010, "H2s Mediates O2 Sensing in the Carotid Body," Proceedings of the National Academy of Sciences U.S.A. 107:10719-10724.
Peng et al., 2011, "A Fluorescent Probe for Fast and Quantitative Detection of Hydrogen Sulfide in Blood," Angew. Chem. Int. Ed. Engl. 50(41):9672-9675.
Peng et al., 2012, "Thiol Reactive Probes and Chemosensors," Sensors (Basel) 12:15907-15946.
Petrizza et al., 2016, "Dye-doped silica nanoparticle probes for fluorescence lifetime imaging of reductive environments in living cells," RSC Advances: An International Journal to Further the Chemical Sciences 6(106):104164-104172.
Qian et al., 2011, "Selective Fluorescent Probes for Live-Cell Monitoring of Sulphide," Nature Communications 2:495.

(56) References Cited

OTHER PUBLICATIONS

Sasakura et al., 2011, "Development of a Highly Selective Fluorescence Probe for Hydrogen Sulfide," J American Chemical Society 133:18003-18005.
Schiavon et al., 1995, "Electrochemical Detection of Trace Hydrogen Sulfide in Gaseous Samples by Porous Silver Electrodes Supported on Ion-Exchange Membranes (Solid Polymer Electrolytes)," Analytical Chemistry 67(2):318-323.
Shamirian et al., 2016, "Ratiometric QD-FRET sensing of aqueous H2S in vitro," Analytical Chemistry 88(11):6050-6056.
Shen et al., 2009, "Poly(ethylene glycol) carbodiimide coupling reagents for the biological and chemical functionalization of water-soluble nanoparticles," ACS Nano 3:915-923.
Varlet et al., 2015, "Hydrogen Sulfide Measurement by Headspace-Gas Chromatography-Mass Spectrometry (Hs-Gc-Ms): Application to Gaseous Samples and Gas Dissolved in Muscle," J. Analytical Toxicology 39:52-57.
Wang et al., 2014, "2,6-Dansyl Azide as a Fluorescent Probe for Hydrogen Sulfide," J. Fluorescence 24:1-5.
Willard et al., 2001, "CdSe-ZnS Quantum Dots as Resonance Energy Transfer Donors in a Model Protein-Protein Binding Assay," Nano Letters 1:469-474.
Yang et al., 2006, "Evaluation of disulfide reduction during receptor-mediated endocytosis by using FRET imaging," Proceedings of the National Academy of Sciences 103(37):13872-13877.
Yu et al., 2013, "Carbon-dot-based ratiometric fluorescent sensor for detecting hydrogen sulfide in aqueous media and inside live cells," Chemical Communications 49(4):403-405.
Zhu et al., 2014, "A two-photon "turn-on" fluorescent probe based on carbon nanodots for imaging and selective biosensing of hydrogen sulfide in live cells and tissues," Analyst 139(8):1945-1951.

* cited by examiner

PVC Modified QDs:

Results

Z-Average (d.nm): 153.0
Pdl: 0.229
Intercept: 0.900
Result quality: Good

| | Size (d.nm): | % Number: | St Dev (d.n... |
|---|---|---|---|
| Peak 1: | 151.0 | 100.0 | 30.31 |
| Peak 2: | 0.000 | 0.0 | 0.000 |
| Peak 3: | 0.000 | 0.0 | 0.000 |

Results

Z-Average (d.nm): 153.0
Pdl: 0.229
Intercept: 0.900
Result quality: Good

| | Size (d.nm): | % Number: | St Dev (d.n... |
|---|---|---|---|
| Peak 1: | 164.6 | 100.0 | 32.556 |
| Peak 2: | 0.000 | 0.0 | 0.000 |
| Peak 3: | 0.000 | 0.0 | 0.000 |

Uncoated QD:

Results

| | Size (d.nm): | % Number: | St Dev (d.n...) |
|---|---|---|---|
| Z-Average (d.nm): 8.277 | Peak 1: 8.277 | 100.0 | 1.911 |
| PdI: 0.181 | Peak 2: 0.000 | 0.0 | 0.000 |
| Intercept: 0.903 | Peak 3: 0.000 | 0.0 | 0.000 |
| Result quality: Refer to quality report | | | |

Results

| | Size (d.nm): | % Number: | St Dev (d.n...) |
|---|---|---|---|
| Z-Average (d.nm): 83.03 | Peak 1: 9.843 | 99.9 | 3.490 |
| PdI: 0.181 | Peak 2: 162.7 | 0.1 | 34.53 |
| Intercept: 0.903 | Peak 3: 0.000 | 0.0 | 0.000 |
| Result quality: Refer to quality report | | | |

RATIOMETRIC QUANTUM DOT-RHODAMINE B SENSING COMPOUND AND DEVICE MADE FROM THE COMPOUND

This application claims priority from U.S. Provisional Patent Application Ser. No. 62/311,148, filed Mar. 21, 2016, which is hereby incorporated by reference in its entirety.

BACKGROUND

Chemically sensitive organic dye reporters have been developed for over 100 years, and research in this area is still active. However, there are few purely organic sensors that are quantitative, selective, and photochemically stable. Many look to nanotechnology to address these issues. Semiconductor quantum dots ("QDs", also known as nanocrystals) are highly attractive for making fluorescence measurements due to their extreme brightness and photostability. Unfortunately, the large size and surface passivation of high quality QDs generally prevent chemical or biological sensitivity.

The use of quantum dots for chemical sensing brings significant advantages over organic-based technology alone due to their unique optical and electronic properties. QD color can be tuned through the effect of quantum confinement, meaning that small QDs have much larger bandgaps compared to large QDs. Furthermore, the chemical composition of the QDs may be altered for the purpose of bandgap engineering and to reduce toxicity. As such, utilizing photochemically stable QDs as chemical and biological sensing agents has become a significant research endeavor.

This photochemical stability actually introduces a problem concerning the use of QDs as sensors, as they intrinsically are insensitive to their environment and thus are poor sensors on their own. However, several research groups, including inventors of the present disclosure, have shown that manipulating energy transfer can impart chemical sensing capability to QDs. In 2001, a paper by Van Orden, et al., first demonstrated efficient Förster Resonant Energy Transfer (FRET) from a QD donor to an organic dye acceptor. Van Orden, A., et al., CdSe—ZnS Quantum Dots as Resonance Energy Transfer Donors in a Model Protein-Protein Binding Assay, *Nano Lett.* 2001, 1, 469-474. Another paper by Mattoussi, et al., showed that QDs can sense chemical agents by designing a CdSe-fluorescence quencher conjugate where the quencher was permanently displaced by trinitrotoluene (TNT). Thus, FRET from the QD to the quencher was removed in the presence of TNT resulting in increased QD emission. Mattoussi, H., et al., A Hybrid Quantum Dot-Antibody Fragment Fluorescence Resonance Energy Transfer-Based TNT Sensor. *J. Am. Chem. Soc.* 2005, 127, 6744-6751. FRET-based sensing was extended to detect biological species such as maltose. Mauro, J. M. et al., Self-Assembled Nanoscale Biosensors Based on Quantum Dot Fret Donors. *Nat. Mater.* 2003, 2, 630-638.

There is an ongoing debate concerning the concentration of hydrogen sulfide in cells, blood, and in tissues. A wide range of 2-300 μM has been reported by different groups, which is likely the result of the use of different sampling techniques and detection methods. Concentrations in the nanomolar range have also been reported. Methods of $H_2S$ detection such as chromatography, colorimetry, and electrochemical assays suffer from poor biological compatibility, and require complicated sample preparation processes. One strategy to address these issues is based on the fact that $H_2S$ dissociates in an aqueous solution to form an equilibrium between $H_2S \leftrightarrow HS^- \leftrightarrow S^{2-}$, where bisulfide ($HS^-$) is favored and is the target analyte "stand-in" for $H_2S$. As such, the design of fluorescent probes for bisulfide have attracted significant attention due to the convenience, compatibility, and sensitivity of fluorescence methods that facilitate the real-time detection of the analyte within biological environments.

Presently, there are several examples of organic-based sulfide-reactive fluorescent probes that function according to strategies based on metal-sulfide interactions, reduction of azide and nitro groups, and nuclephilic addition. Detailed mechanisms and discussion of these systems can be found in recent reviews, such as Jiang, L. et al., Fluorescence Chemosensors for Hydrogen Sulfide Detection in Biological Systems. *Analyst* 2015, 140, 1772-1786; and Wang, B. et al., Thiol Reactive Probes and Chemosensors. *Sensors (Basel)* 2012, 12, 15907-15946. These examples demonstrate sensing organic dyes that brighten in the presence of $HS^-$. However, this single response to the analyte is difficult to calibrate within complex biological environments and may have unknown interactions with other species. This issue is addressed by the use of ratiometrically reporting chromophores, which change color in the presence of the analyte. These systems have an isosbestic point allowing the sensor to be calibrated by measuring the ratio of intensity at any two wavelengths, which is unique for the concentration of the analyte. As a result, the spectrum of the probe provides the analytical metric, rather than the fluorescent probe intensity. While ratiometric or 'self-calibrating' fluorescent organic dyes that sense $HS^-$ have been reported, the use of these materials may require complex and costly excitation schemes. Furthermore, all organic chromophores are prone towards photobleaching.

A novel ratiometric sensing agent that addresses one or more of the concerns with conventional sensing agents, as discussed above, would be considered a valuable addition to the art.

BRIEF SUMMARY 1.01 The present disclosure is directed to a sensing agent. The sensing agent comprises a quantum dot; and a dye moiety coupled to the quantum dot. The sensing agent is capable of sensing at least one analyte chosen from hydrogen sulfide ($H_2S$) and bisulfide.

1.02 The sensing agent of 1.01, wherein the dye moiety is coupled to the quantum dot via a coupling moiety that is cleavable by the at least one analyte.

1.03 The sensing agents of any of 1.01 to 1.02, wherein the sensing agent is capable of exhibiting a ratiometric response to at least one analyte chosen from hydrogen sulfide ($H_2S$) and bisulfide 1.04 The sensing agents of any of 1.01 to 1.03, wherein the coupling moiety comprises a disulfide bridge.

1.05 The sensing agents of any of 1.01 to 1.04, wherein the sensing agent has the formula:

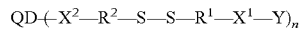

wherein:
QD is the quantum dot,
Y is the dye moiety,
$R^1$ and $R^2$ are organic bridging groups that will, in combination with the associated linkages $X^1$ and $X^2$ and disulfide bond (—S—S—), provide a distance between the dye and the QD that is the same as the Förster distance or less, and X[1] and X[2] are linkages that respectively function to attach the R[1] group to the dye and R[2] group to the quantum dot; and n is the number of coupling-dye groups attached to the QD.

1.06 The sensing agents of any of 1.01 to 1.05, wherein the quantum dot comprises an emissive material selected from ZnS, ZnSe, ZnSe/ZnS, CdS, CdS/ZnS, CdZnS, CdZnS/ZnS, CdSe, CdZnSe, CdSeS, CdZnSeS, CdSe/ZnS, CdZnSe/ZnS, CdSeS/ZnS, CdZnSeS/ZnS, CdSe/CdZnS, CdZnSe/CdZnS, CdSeS/CdZnS, CdZnSeS/CdZnS, CdTe, CdSeTe, CdTe/ZnS, CdSeTe/ZnS, CdTe/CdZnS, CdSeTe/CdZnS, CdTe/ZnSe, CdSeTe/ZnSe, CdTe/ZnSeS, CdSeTe/ZnSeS, ZnSe/CdS, CdS/ZnSe, ZnSe/CdS/ZnS, CdS/ZnSe/ZnS, CdSe/CdTe, CdTe/CdSe, CdSe/CdTe/ZnS, CdTe/CdSe/ZnS, CdSe/CdTe/ZnSe, CdTe/CdSe/ZnSe, AgInS$_2$, AgInS$_2$/ZnS, CuInS$_2$, CuInS$_2$/ZnS, AgInSe$_2$, AgInSe$_2$/ZnS, CuInSe$_2$, CuInSe$_2$/ZnS, ZnSe:Mn, ZnSe:Mn/ZnS, ZnSe:Cu, ZnSe:Cu/ZnS, ZnSe/ZnMnS/ZnS, CdSe:Ag, CdSe:Ag/ZnS, PbS, PbS/ZnS, PbSe, PbSe/CdSe, PbSe/CdSe/ZnSe, ZnSe/ZnMgS/ZnS, ZnSeMn$_x$/ZnS, CdS/Cd$_x$Zn$^{(1-x)}$S, CdSe/Cd$_x$Zn$_{(1-x)}$S, CdSe$_x$Te$_{(1-x)}$/Cd$_y$Zn$_{(1-x)}$S, AgInS$_2$/ZnS, CuInS$_2$/ZnS, AgInSe$_2$/ZnS, and CuInSe$_2$/ZnS, where x and y range from 0 to 1.

1.07 The sensing agents of any of 1.01 to 1.06, wherein the quantum dot comprises at least one coating chosen from a phase transfer coating, a ligand exchange coating, a polymer coating and a silanization coating.

1.08 The sensing agents of any of 1.01 to 1.07, wherein the dye moiety is a fluorescent dye group selected from a coumarin group, a xanthene group, a BODIPY group, an ALEXA group, a squaraine group, a cyanine group, a quantum dot, a quenching dye group, an azide-functional dye group, a genetically encoded azide dye group, a ratiometric azide dye group, a self-reactive dye group, a nitro-functional dye group, a nucleophilic displacement dye group, a ratiometric nucleophilic addition dye group, a disulfide exchange dye group, a michael addition dye group and a copper reactive dye group.

1.09 The sensing agents of any of 1.01 to 1.08, wherein the dye moiety is a rhodamine group selected from one of:

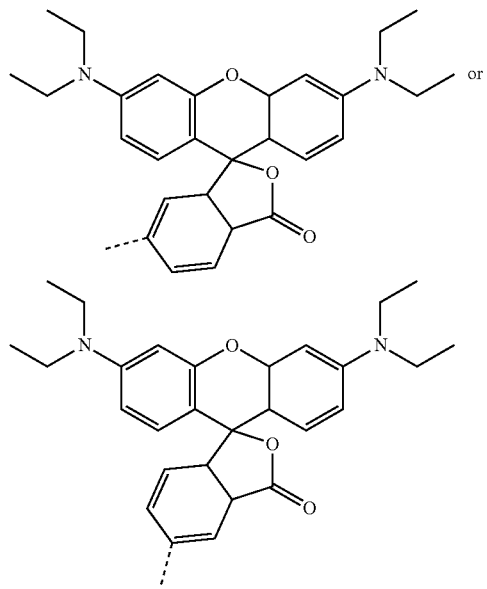

or where the dotted bond shows the position of attachment to the coupling moiety.

1.10 The sensing agents of any of 1.05 to 1.09, wherein R[1] and R[2] are alkyl bridges and X[1] and X[2] are amide linkages.

2.01 The present disclosure is also directed to a sensor. The sensor comprises a support matrix; and a sensing agent embedded in the support matrix. The sensing agent comprises a quantum dot; and a dye moiety coupled to the quantum dot. The sensing agent is capable of sensing at least one analyte chosen from hydrogen sulfide and bisulfide.

2.02 The sensor of 2.02, wherein the sensing agent is capable of exhibiting a ratiometric response to at least one analyte chosen from hydrogen sulfide ($H_2S$) and bisulfide.

2.03 The sensors of any of 2.01 to 2.02, wherein the support matrix is chosen from paper, a polymer and a combination thereof.

2.04 The sensors of any of 2.01 to 2.03, wherein the dye moiety is coupled to the quantum dot via a coupling moiety that is cleavable by the at least one analyte.

2.05 The sensor of 2.04, wherein the coupling moiety comprises a disulfide bridge.

The sensors of any of 2.01 to 2.05, wherein the sensing agent has the formula:

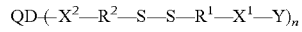

wherein:
QD is the quantum dot,
Y is the dye moiety,
R[1] and R[2] organic bridging groups that will, in combination with the associated linkages X[1] and X[2] and disulfide bond (—S—S—), provide a distance between the dye and the QD that is the same as the Förster distance or less, and
X[1] and X[2] are linkages that respectively function to attach the R[1] group to the dye and R[2] group to the quantum dot;
n is the number of coupling-dye groups attached to the QD.

2.07 The sensors of any of 2.01 to 2.06, wherein the quantum dot comprises an emissive material selected from ZnS, ZnSe, ZnSe/ZnS, CdS, CdS/ZnS, CdZnS, CdZnS/ZnS, CdSe, CdZnSe, CdSeS, CdZnSeS, CdSe/ZnS, CdZnSe/ZnS, CdSeS/ZnS, CdZnSeS/ZnS, CdSe/CdZnS, CdZnSe/CdZnS, CdSeS/CdZnS, CdZnSeS/CdZnS, CdTe, CdSeTe, CdTe/ZnS, CdSeTe/ZnS, CdTe/CdZnS, CdSeTe/CdZnS, CdTe/ZnSe, CdSeTe/ZnSe, CdTe/ZnSeS, CdSeTe/ZnSeS, ZnSe/CdS, CdS/ZnSe, ZnSe/CdS/ZnS, CdS/ZnSe/ZnS, CdSe/CdTe, CdTe/CdSe, CdSe/CdTe/ZnS, CdTe/CdSe/ZnS, CdSe/CdTe/ZnSe, CdTe/CdSe/ZnSe, AgInS$_2$, AgInS$_2$/ZnS, CuInS$_2$, CuInS$_2$/ZnS, AgInSe$_2$, AgInSe$_2$/ZnS, CuInSe$_2$, CuInSe$_2$/ZnS, ZnSe:Mn, ZnSe:Mn/ZnS, ZnSe:Cu, ZnSe:Cu/ZnS, ZnSe/ZnIVInS/ZnS, CdSe:Ag, CdSe:Ag/ZnS, PbS, PbS/ZnS, PbSe, PbSe/CdSe, PbSe/CdSe/ZnSe, ZnSe/ZnNIgS/ZnS, ZnSeMn$_x$/ZnS, CdS/Cd$_x$Zn$_{(1-x)}$S, CdSe/Cd$_x$Zn$_{(1-x)}$S, CdSe$_x$Te$_{(1-x)}$/Cd$_y$Zn$_{(1-y)}$S, AgInS$_2$/ZnS, CuInS$_2$/ZnS, AgInSe$_2$/ZnS, and CuInSe$_2$/ZnS, where x and y range from 0 to 1.

2.08 The sensors of any of 2.01 to 2.07, wherein the quantum dot comprises at least one coating chosen from a phase transfer coating, a ligand exchange coating, a polymer coating and a silanization coating.

2.09 The sensors of any of 2.01 to 2.08, wherein the dye moiety is a fluorescent dye group selected from a coumarin group, a xanthene group, a BODIPY group, an ALEXA group, a squaraine group, a cyanine group, a quantum dot, a quenching dye group, an azide-functional dye group, a genetically encoded azide dye group, a ratiometric azide dye group, a self-reactive dye group, a nitro-functional dye group, a nucleophilic displacement dye group, a ratiometric nucleophilic addition dye group, a disulfide exchange dye group, a michael addition dye group and a copper reactive dye group.

2.10 The sensors of any of 2.01 to 2.09, wherein the dye moiety is a rhodamine group selected from one of:

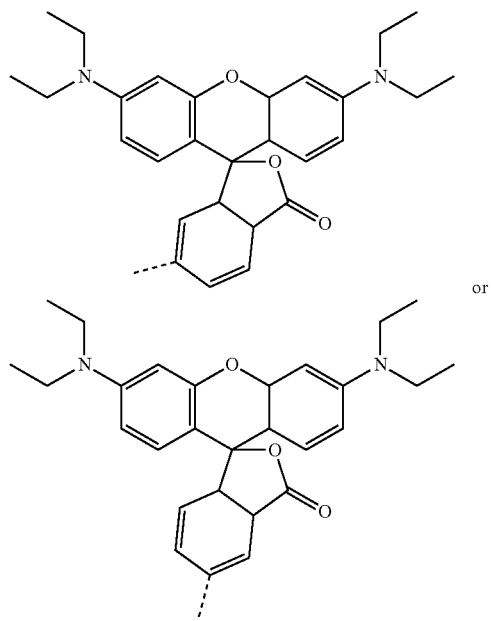

where the dotted bond shows the position of attachment to the coupling moiety.

2.11 The sensors of any of 2.01 to 2.10, wherein the sensor has a detection limit for bistilfide, in water, of less than 2 µM at a sensor concentration of $3.4 \times 10^{-9}$ M as determined by the boot strap method, where the conjugated dye:QD ratio is 1.3:1.

2.12 The sensors of any of 2.01 to 2.11, wherein the sensor is selective towards the HS$^-$ anion compared to other thiols chosen from glutathione and cysteine.

2.13 The sensors of any of 2.01 to 2.12, wherein the sensor provides for a linear correlation of the integrated emission ratio of the QD:dye as a function of the HS$^-$ concentration over a broader range of bisulfide analyte concentrations then the same QD donor and dye acceptor combination without the disulfide bridge.

2.14 The sensor of any of claims 2.06 to 2.13, wherein $R^1$ and $R^2$ are alkyl bridges and $X^1$ and $X^2$ are amide linkages.

Further areas of applicability of the present invention will become apparent from the detailed description provided hereinafter. It should be understood that the detailed description and specific examples, while indicating some preferred aspects of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
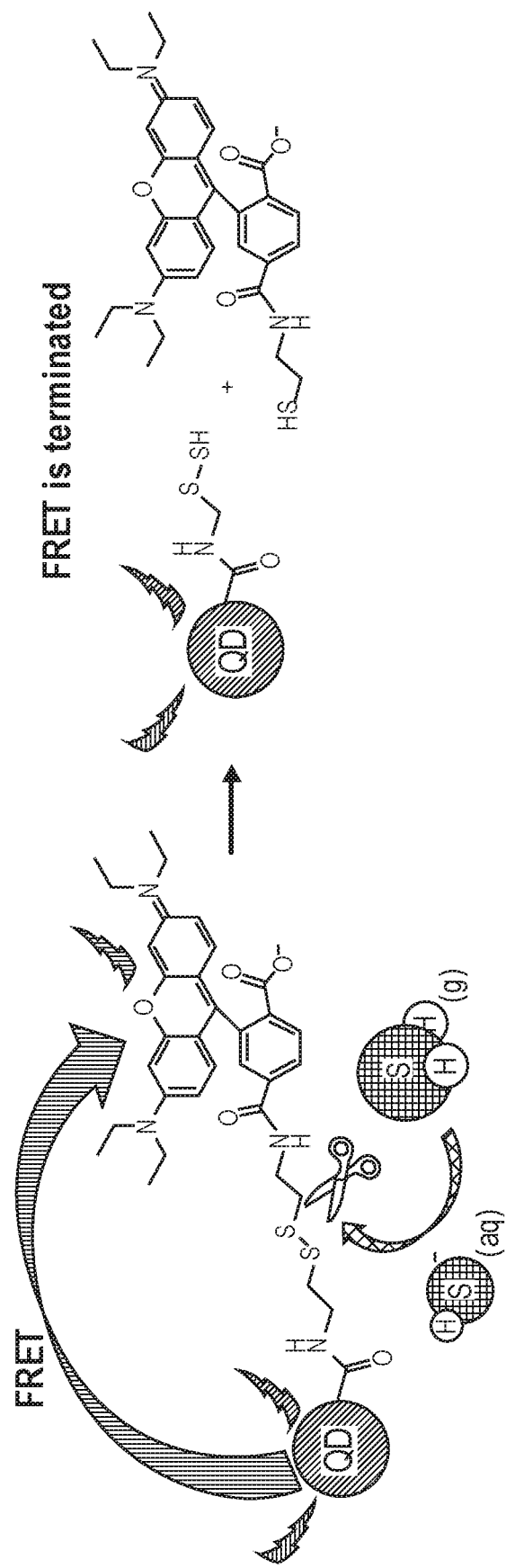
FIG. 1 illustrates an example of a ratiometric sensing agent and the response mechanism of the sensing agent based on Förster Resonant Energy Transfer (FRET) modulation, according to an embodiment of the present disclosure.

The following description of various preferred aspect(s) is merely exemplary in nature and is in no way intended to limit the invention, its application, or uses.

As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight. The amounts given are based on the active weight of the material.

The present disclosure is directed to a dye functionalized quantum dot ("QD") that acts as a sensing agent for detection of gas and/or HS⁻ (also known as bisulfide). In aqueous solution the $H_2S$ gas is in equilibrium with aqueous HS⁻. In an embodiment, the QD acts as a donor and the dye as an acceptor to form a QD-dye conjugate that functions to provide a FRET-based sensing mechanism. Energy transfer efficiency from the QD donor to the dye acceptor is modulated when environmental factors, such as pH or the presence of elements such as HS⁻, alter the dye optical properties or change the spatial distance between the QD and dye. Consequently, the emission of the construct has a ratiometric, or "color-changing" response, toward targeted analytes. A ratiometric sensor is superior to a single-emission turn on or off sensor as the shift in color, rather than a reduction or enhancement in light intensity, may allow for the visual or instrumental detection of extremely low levels of hydrogen sulfide or bisulfide. In addition to sensing hydrogen sulfide in a biological or cellular environment, this would also be useful to sense hydrogen sulfide in other applications and environments, such as in breath. Hydrogen sulfide contributes significantly to malodor in breath and can be detected by the human nose at parts-per-billion levels.

Due in part to their ability for ratiometrically sensing sulfide and/or disulfide, the QD-dye conjugate sensing agents of the present disclosure address one or more of the above described issues of conventional sensing techniques. For example, the continuous and strong absorption profiles of the QDs result in an excitation-wavelength independent response. As such, QD-dye conjugates do not need multiple excitation sources (or excitation at a single, specific absorptive isosbestic point) to properly function, as do conventional, radiometrically reporting, fluorescent organic dyes that do not include a QD. QD-dye conjugates can also be resistant to photobleaching through the attachment of multiple dye moieties to a single QD. Thus, the QD-dye conjugate sensing agents of the present disclosure have resolved one or more weaknesses of conventional ratiometric dye based sensors.

An embodiment of the present disclosure is directed to a sensing agent. The sensing agent comprises a quantum dot and a dye moiety coupled to the quantum dot. The sensing agent is capable of sensing, such as by exhibiting a ratiometric response to, at least one analyte chosen from hydrogen sulfide and bisulfide.

The dye moiety is coupled to the quantum dot via a coupling moiety. In cases where a dye is sensitive to hydrogen sulfide and/or bisulfide and can function as an acceptor with the QD donor, any suitable coupling moiety can potentially be employed. In an embodiment, the coupling moiety is cleavable by the at least one analyte. For example, the coupling moiety can comprise a disulfide bridge (e.g., —R—S—S—R— group where R is an alkyl or other group) that provides sensitivity to at least one analyte chosen from hydrogen sulfide ($H_2S$) and bisulfide. In addition, the coupling moiety can include terminal anchor groups, such as amide linkages, that function to attach to the QD and dye moiety. Examples of such a sensing agent can include compounds of the Formula 1:

$$QD\text{---}(\text{---}X^2\text{---}R^2\text{---}S\text{---}S\text{---}R^1\text{---}X^1\text{---}Y)_n \quad (1)$$

wherein:

QD is the quantum dot;

Y is the dye moiety;

$R^1$ and $R^2$ are any organic bridging groups that will, in combination with the associated linkages $X^{1e}$ and $X^2$ and disulfide bond (—S—S—), provide a distance between the dye and the QD that is the same as the Förster distance or less;

$X^1$ and $X^2$ are linkages that respectively function to attach the $R^1$ group to the dye and $R^2$ group to the quantum dot; and n is the number of coupling-dye groups attached to the QD.

In an embodiment, $R^1$ and $R^2$ can be the same or different, and can be chosen from substituted or unsubstituted, saturated or unsaturated, linear, branched or cyclic $C_1$ to $C_{10,000}$ aliphatic or aromatic groups optionally having one or more heteroatoms, such as nitrogen, oxygen, sulfur, phosphorus, or halogen, where if $R^1$ and $R^2$ are substituted, the substituent can be any desired substituent, such as alkyl, alkoxy, ether, aryl, alkenyl, alkynyl, halogen, halo, hydroxyl, carbonyl, aldehyde, carboxyl, carboxyl ester, amide, amine or any other desired substituent. $R^1$ and $R^2$ can have any desired number of carbon atoms that result in the coupling moiety having the desired length, such as 1 to 10,000 carbon atoms, or 2 to 1000 carbon atoms, 2 to 100 carbon atoms or 2 to 20 carbon atoms. Examples of $R^1$ and $R^2$ include linear aliphatic groups such as n-alkyl bridges having 1 to 10,000 carbon atoms, such as 2 to 20 carbon atoms or 2 to 6 carbon atoms. Further examples include polymer linker groups, DNA groups and peptide groups. Example peptides include the use of a cysteine residue in a peptide linker, which can be functionalized with maleimide reagents. Furthermore, the natural amine and carboxylic groups of a peptide's N- and P-termini may function to form the amide linking $X^1$ and $X^2$ groups discussed below when attached to the dye and QD.

Examples for $X^1$ and $X^2$ include amide linkages or any other chemical moiety that serves a similar purpose. The amide linkages can be made using carboxy coordinating groups and an amine terminated linker, such as by the method shown in Example 1 below, or by any other suitable method. Other examples of groups that can be used to form $X^2$ for attachment to the quantum dot include QD-surface coordinating ligands such as histidine, thiol, poly(histidine) and poly(thiol) functional groups to attach directly to the QD surface; a poly(cation) such as poly(arginine) or poly(lysine) functional groups for attachment to anionic QDs; biotin functional groups to attach to streptavidin functionalized QDs; amine functional groups to conjugate to carboxylic acid or n-hydroxysuccinimide coated QDs; thiols to conjugate to maleimide or iodoacetimide functional QDs; or isocyanate or isothiocyanate to coordinate to amine or hydroxyl functional QD surfaces. Examples of coordinator groups attached to the dye that can be used to form $X^1$, include: carboxylic acid, isocyanate or isothiocyanate functional groups to conjugate to amine functional dyes; amine or hydroxyl functional groups to conjugate to carboxylic acid, isocyanate, or isothiocyanate functional dyes; thiol functional groups to coordinate to maleimide or iodoacetimide functional dyes. Still other example functional $X^1$ and $X^2$ linkages can be employed, including any suitable linkages known in the art.

Values for "n" in Formula 1 can be any desired number. Example ranges include from 1 to 1000, such as 1 to 200 or 1 to 130 or 1 to 10 or 1 to 2.

The Förster distance may vary depending on the particular quantum dot/dye conjugate pair that is employed. As an example, the Förster distance may range from about 10 nm or less, such as 0.1 nm to about 10 nm, such as about 2 nm to about 7 nm, such as about 5 nm. One of ordinary skill in the art would be readily able to determine the Förster distance for any given QD/dye conjugate pair without undue experimentation.

The response mechanism for sensing agents of the present disclosure that include the disulfide bridge is based on the reducing ability of hydrogen sulfide ($H_2S$) and/or the bistilfide ion, which can cleave the disulfide bond connecting the QD to the dye. This results in a loss of Förster Resonant Energy Transfer (FRET) between the emitting QD donor and the dye acceptor, thereby producing a ratiometric fluorescence response to the presence of hydrogen sulfide and/or bisulfide. Since cleavage of a disulfide bond by $HS^-$ is facile, linking a dye to a QD via a disulfide bridge can be incorporated within a ratiometric fluorescent sensing strategy.

The ability to provide a linear correlation between the integrated emission ratio of the QD:dye as a function of $H_2S$ and/or $HS^-$ analyte concentration is beneficial because it can allow improved accuracy and sensitivity for measuring H2S/HS-concentrations. In the case of dyes such as rhodamine, which provide intrinsic sensitivity to hydrogen sulfide and/or bisulfide analytes, incorporating the disulfide bridge into the QD/Dye sensor can allow for a linear correlation of the integrated emission ratio of the QD:dye as a function of the HS" concentration over a broader range of $H_2S$ and/or HS analyte concentrations then the same QD donor and dye acceptor combination without the disulfide bridge. Increasing the linear correlation range provides for increased sensitivity and accuracy for measuring a broader range of $H_2S/HS^-$ concentrations. In an embodiment, the QD/dye sensors that include the disulfide bridge can exhibit a linear correlation of the integrated emission ratio of the QD:dye as a function of the $HS^-$ concentration over a range of, for example, between 0 to about 50 or 60 μM of $HS^-$ or more, as shown in the examples and data provided below.

FIG. 1 shows an example of a mechanism for cleavage, involving a carboxyrhodamine B derivative with a coupling moiety containing a disulfide bond. The rhodamine dye chromophore can act as an acceptor for a green-emitting water-soluble quantum dot donor after coupling the two together, as discussed in greater detail below. As shown in FIG. 1, the disulfide bond cleaves upon exposure to $HS^-$, causing the dye to diffuse away from the QD and terminating FRET. In this sensing motif, any QD that can act as a donor to an energy accepting chromophore, where the two are connected via a cleavable disulfide bond, will function as a $HS^-$ sensor via a similar mechanism to that shown in FIG. 1. Thus, in addition to providing for an increased linear correlation of the integrated emission ratio of the QD:dye as a function of the $HS^-$ concentration, as discussed above, use of a disulfide bridge containing coupler can also increase the range of dyes that can be coupled to a QD to form a ratiometric sensing agent.

The quantum dot employed in of any of the sensing agents of the present disclosure, including those of Formula 1, can be made of any material that is capable of acting as a donor with the particular dye acceptor to which it will be linked so as to provide for Förster Resonant Energy Transfer (FRET) and the associated analyte detection response. Generally, this means that the quantum dot material will be selected to emit radiation at a shorter (higher energy) wavelength relative to the wavelength emitted by the dye moiety. Depending on the application, the quantum dot can be chosen to emit radiation at any suitable wavelength, including infrared, visible and UV, assuming the dye is chosen to provide a lower energy emission. According to an embodiment of the present disclosure, both the quantum dot material and the dye moiety can be chosen to emit visible radiation, each at sufficiently different colors so as to provide a ratiometric change of color that is suitable for indicating analyte concentration. Sensing agents and sensors formed therefrom where the QD and/or dye are chosen so as not to emit light in the visible spectrum may not provide a ratiometric response in the visible color spectrum.

Examples of suitable quantum dot emissive materials for the QD of any of the sensing agents of the present disclosure, including those of Formula 1, include any of the materials selected from ZnS, ZnSe, ZnSe/ZnS, CdS, CdS/ZnS, CdZnS, CdZnS/ZnS, CdSe, CdZnSe, CdSeS, CdZnSeS, CdSe/ZnS, CdZnSe/ZnS, CdSeS/ZnS, CdZnSeS/ZnS, CdSe/CdZnS, CdZnSe/CdZnS, CdSeS/CanS, CdZnSeS/CdZnS, CdTe, CdSeTe, CdTe/ZnS, CdSeTe/ZnS, CdTe/CdZnS, CdSeTe/CdZnS, CdTe/ZnSe, CdSeTe/ZnSe, CdTelThSeS, CdSeTe/ZnSeS, ZnSe/CdS, CdS/ZnSe, ZnSe/CdS/ZnS, CdS/ZnSe/ZnS, CdSe/CdTe, CdTe/CdSe, CdSe/CdTe/ZnS, CdTe/CdSe/ZnS, CdSe/CdTe/ZnSe, CdTe/CdSe/ZnSe, $AgInS_2$, $AgInS_2/ZnS$, $CuInS_2$, $CuInS_2/ZnS$, $AgInSe_2$, $AgInSe_2/ZnS$, $CuInSe_2$, $CuInSe_2/ZnS$, ZnSe:Mn, ZnSe:Mn/ZnS, ZnSe:Cu, ZnSe:Cu/ZnS, ZnSe/ZnMnS/ZnS, ZnSe/ZnMgS/ZnS, CdSe:Ag, CdSe:Ag/ZnS, PbS, PbS/ZnS, PbSe, PbSe/CdSe, and PbSe/CdSe/ZnSe. In an embodiment, the materials are selected from CdSe/CdZnS, CdSe/ZnS, ZnSe/ZnMgS/ZnS, CdTe/ZnS, PbS/ZnS, $ZnSeMn_x/ZnS$ (x: 0→1), $CdS/Cd_xZn_{(1-x)}S$ (x: 0→1), $CdSe/Cd_xZn_{(1-x)}S$ (x: 0→1), $CdSe_xTe_{(1-x)}/Cd_yZn_{(1-y)}S$ (x,y: 0→1), $AgInS_2/ZnS$, $CuInS_2/ZnS$, $AgInSe_2/ZnS$, and $CuInSe_2/ZnS$. In yet another embodiment, the materials are selected from $ZnSeMn_x/ZnS$ (x: 0→1), $CdS/Cd_xZn_{(1-x)}S$ (x: 0→1), $CdSe/Cd_xZn_{(1-x)}S$ (x: 0→1), $CdSe_xTe_{(1-x)}/Cd_yZn_{(1-y)}S$ (x,y: 0→1), $AgInS_2/ZnS$, $CuInS_2/ZnS$, $AgInSe_2/ZnS$, and $CuInSe_2/ZnS$.

Figure 2:
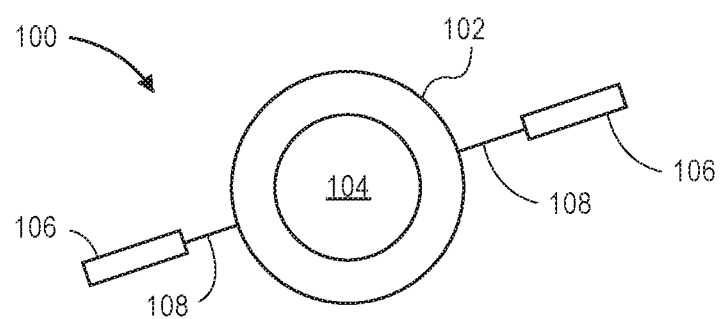
FIG. 2 illustrates an example of a ratiometric sensing agent incorporating a coated. QD, according to an embodiment of the present disclosure.

In an embodiment, the quantum dot comprises at least one coating that can reduce quantum dot quenching by hydrogen sulfide. FIG. 2 illustrates an example of a sensing agent 100 comprising a coating 102 on a quantum dot 104. Dye moieties 106 and linkers 108 are also shown. Quantum dot quenching can be caused by hydrogen sulfide and/or bisulfide ions attaching to the quantum dot surface, where the hydrogen sulfide and/or bisulfide can act to absorb energy from the quantum dot that would otherwise be emitted as radiation, either from the QD itself or from the dye via FRET. The coating 102. reduces the ability of the hydrogen sulfide/bisulfide to attach to the QD and/or absorb energy therefrom, thereby reducing or avoiding the problem of quenching. As examples, the polymer dot can include at least one coating 102 selected from a phase transfer coating, a ligand exchange coating, a polymer coating and a silanization coating. Specific examples of such types of coatings include: Phase transfer coatings made from Tetraoctylammonium bromide (TOAB), Cetyltrimethylammonium chloride, Octadecyl-p-vinyl-benzyldimethylammonium chloride and combinations thereof; Ligand exchange coatings made from Mercaptoacetic acid (MAA), mercaptopropionic acid (MPA), mercaptoundecanoic acid (MUA), Mercaptosuccinic acid (MSA), Dihydrolipoic acid (DHLA), Modified DHLA and combinations thereof; Polymer coatings made from: Poly(acrylic acid) (PAA); modified poly (acrylic acid), Poly(maleic anhydride alt-1-tetradecene), Poly(maleic anhydride alt-1-octadecene), modified Poly(maleic anhydride), Poly(acryloyoxysuccinimide) (PAAS), Poly (methyl methacrylate) (PMMA), Poly(2-(dimethylamino)ethyl methacrylate) (PDMAEMA), Poly(allylamine) (PAL), Poly (ethylenimine) (PEI), Poly(amidoamine) (PAMAM), Poly (acrylamide) (PAM) Poly(N-isopropylacrylamide) (PNIPAM), Poly(N-vinylcaprolactam) (PVCL), Poly (caprolactone) (PCL), Chitosan, Amphiphilic PEG polymers, Poly(vinylsulfonic acid) (PVSA), Polylysine (PL)/dextran, Poly(styrene sulfonate) (PSS), Poly(lactide) (PLA), Cellulose triacetate (CTA), Poly(lauryl methacrylate) (PLMA), Poly(lauryl methacrylate-co-ethylene glycol dimethacrylate) (P(LMA-co-EGDM), Nylon, Polyvinyl chloride (PVC) and combinations thereof; Silanization coatings, such as silica shells and silane passivation coatings. Examples for making phase transfer coatings, ligand exchange coatings, polymer coatings and silanization coatings from the above listed materials are known in the art.

The dye moiety of any of the sensing agents of the present disclosure, including those of Formula 1, can be made using any dye that can be coupled to a quantum dot, as described herein, so as to exhibit FRET and provide the desired ratiometric response to detect the presence of, and or concentration of, at least one species chosen from hydrogen sulfide and bisulfide. In an embodiment, the dye moiety is a fluorescent dye moiety made from a dye selected from the following fluorescent dye families: coumarin, xanthene including fluorescein and rhodamine, BODIPY, ALEXA, squaraine and cyanine, and quantum dots. Any of the quantum dots disclosed here can also be used as the dye moiety. Specific examples of rhodamine dyes include rhodamine B, tetramethyl rhodamine, Rhodamine 6G and Rhodamine 101. Other examples of suitable dyes include quenching dyes, such as black hole and gold nanoparticles, and derivatives of the same.

Still other example dyes of any of the sensing agents of the present disclosure, including those of Formula 1, include any intrinsically sulfide-reactive dyes that may be conjugated to quantum dots, such as azide-functional dyes, genetically encoded azide dyes, ratiometric azide dyes, self-reactive dyes, nitro-functional dyes, nucleophilic displacement dyes, ratiometric nucleophilic addition dyes, disulfide exchange dyes, michael addition dyes and copper reactive dyes. Examples of such dyes include: Azide-functional Dyes, such as: Fluorescein, Dansyl azide, Fluorescein-dipicolylamine, Fluorescein-thiosalicylic acid, Fluorescein-azide, Coumarin-azide, 2-(2-aminophenyl) benzothiazole-azide, 7-nitrobenz-2-oxa-1,3-diazole-azide, Dicyanomethylenedihydrofuran-azide, Resorufamine-azide, BODIPY-azide, Phenanthroimidazole-azide, 1,8-naphthalimide azide and derivatives, Luminol-azide, Dicyanomethylene-4 H-chromene-azide, 7-(benzo[d]thiazol-2-yl)-9,9-(2-methoxyethoxy)ethyl-9H-fluorene-azide and Tetraphenylethene-azide; Genetically Encoded Azide Dyes, such as: cpGFP; Ratiometric Azide Dyes, such as: Cyanine-azide, Cresyl violet-azide and 4-azido-1,8-Naphthalimide-azide; Self-reactive Dyes, such as: Coumarin, 6-(benzo[d]thiazol-2'-yl)-2-(methylamino)naphthalene-4-azidobenzyl carbamate, 2-(2'-hydroxyphenypbenzothiazole-p-azidobenzene, Fluorescein-thiourea-DABCY, 1,8-Naphthalimide-p-azidobenzene and Nitro-functional 1,8-naphthalimide; Nitro-functional Dyes, such as: Nitro-functional 1,8-naphthalimide, Nitro-cyanine and. Nitro-coumarin; Nucleophilic Displacement Dyes, such as: 1,8-naphthalimide, Fluorescein, Coumarin, Nile Red, BODIPY, Adamantyl dioxetane, Cyanine, DNP-hydroxycoumarin-piperazine-tetraethylrhodamine, N-alkylmorpholino-1,8-naphthalimide, 4'-dimethylamino-3-hydroxyflavone-dinitrophenyl ether, Aminobenzenethiol-2-hydroxy-5-methylbenzene and Coumarin-piperazine-NBD; Ratiometric Nucleophilic Addition Dyes, such as: Cyanine; Disulfide Exchange Dyes, such as: Coumarin, Resorufin, Fluorescein and 1-IBT; Michael Addition Dyes, such as: 1,3,5-triaryl-2-pyrazoline-BODIPY, Fluorescein and Cyanine; Copper Reactive Dyes, such as: Copper (II)-1-(2-pyridylazo)-2-naphthol, Fluorescein, Anthracene, Phenanthrene-fused dipyrromethene and a Carbon quantum dot.

Any of the dye compounds listed herein can be used to form the dye moieties of the present disclosure. The terms "dye moiety" or "dye group" are defined herein to mean the group of atoms incorporated into the sensing agent from the corresponding dye compound. Any of the above listed dye names can therefore be modified with the term "group" or "moiety" to refer to the corresponding dye moiety or dye group. Thus, the dye moieties formed from the above listed fluorescent dyes or dye families are termed fluorescent dye groups, such as: a coumarin group; a xanthene group, such as a fluorescein group or a rhodamine group (e.g., rhodamine B group, tetramethyl rhodamine group, Rhodamine 6G-group and Rhodamine 101 group); a BODIPY group; an ALEXA group; a squaraine group; and a cyanine group. Other dye groups can include quenching dye groups, azide-functional dye groups, genetically encoded azide dye groups, ratiometric azide dye groups, self-reactive dye groups, nitro-functional dye groups, nucleophilic displacement dye groups, ratiometric nucleophilic addition dye groups, disulfide exchange dye groups, michael addition dye groups and copper reactive dye groups. A "dye moiety" or "group" can be the same as the dye compound itself except for changes made during the chemical process attaching the dye to the QD via the linker, which may include, for example, replacing a hydrogen or some other atom of the dye with a covalent bond shared with the coupling moiety, or reduction of an unsaturated bond of the dye (e.g., reducing a double bond to a single bond) when forming a covalent bond with the coupling moiety. For example, a Rhodamine B dye group may be the same as the Rhodamine B dye minus a hydrogen atom at the position of the covalent bond, as indicated by the dotted lines in the rhodamine group formulae below. Thus, in an embodiment, the dye moiety is a Rhodamine B dye group selected from one of:

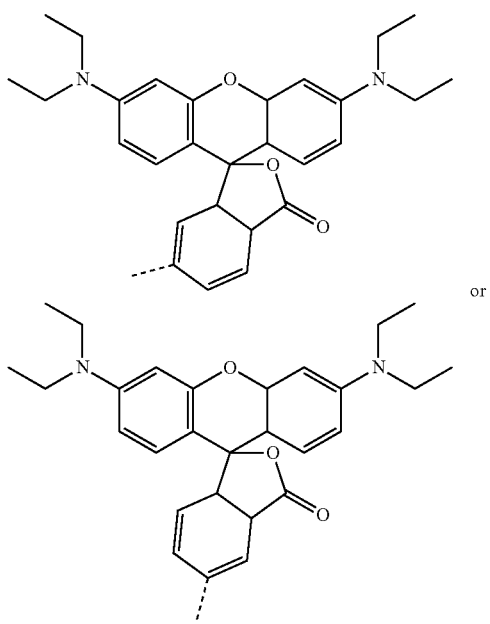

where the dotted bond shows the position of attachment to the coupling moiety.

As described herein, the dye can have a longer emission wavelength than the QD. Where a visible, ratiometric response is desired, the dye, as well as the QD, can have emission wavelengths in the visible spectrum. However, the emission wavelengths of the QD and dye do not always have to be in the visible spectrum. For example, emission wavelengths of either or both of the QD and the dye can be in the UV or infrared range, depending on the particular application, such as may be the case for some medical imaging applications that work best in near-Infrared wavelengths.

In an alternative embodiment, there is no FRET interaction between the dye and the QD. Rather, the QD and dye can be co-excited with a particular excitation wavelength that is chosen to cause emission from both the QD and dye. This QD/dye motif can function in the case where the dye emission is dependent on the analyte concentration without FRET interaction, so that a relatively high analyte concentration can result in a different combined emission ratio of the QD and dye than a low analyte concentration at the chosen excitation wavelength. Because FRET interaction is not employed, the QD-dye sensor can include a dye that emits at a higher wavelength (greater energy) or lower wavelength than the QD. Co-excitation would cause both QD and dye emission, regardless of whether the two were conjoined or not. Further, for conjoined non-FRET systems where QD and dye are simultaneously excited, and sensing is based on the dye component responding to the analyte, the dot and dye can be tethered along any length scale. Thus, the distance between the quantum dot and the dye can be any desired distance and is not limited by the Förster distance.

The non-FRET sensing agents can employ any of the QDs described herein for the FRET sensing agents. The dye can be any dye that is reactive with the bisulfide or hydrogen sulfide analyte. Thus, any dyes disclosed herein that are reactive with the bisulfide or hydrogen sulfide analyte can be used, such as, for example, Rhodamine B. Further, the QD and dye can be linked by any desired coupling moiety. As an example, for non-FRET sensing agents, the —$X^2$—$R^2$—S—S—$R^1$—$X^1$— moiety of Formula 1 above could be replaced with —$X^2$—R—$X^1$—, where $X^2$ and $X^1$ are defined as described for Formula 1 above, and R can be any organic linking group. For example, R can be chosen from substituted or unsubstituted, saturated or unsaturated, linear, branched or cyclic aliphatic or aromatic groups optionally having one or more heteroatoms, such as nitrogen, oxygen, sulfur, phosphorus or halogen, where if R is substituted, the substituent can be any desired substituent, such as alkyl, alkoxy, ether, aryl, alkenyl, alkynyl, halogen, halo, hydroxyl, carbonyl, aldehyde, carboxyl, carboxyl ester, amide, amine or any other desired substituent. R can have any desired number of carbon atoms, such as 1 to 100,000 carbon atoms, or 1 to 10,000 carbon atoms, or 2 to 1000 carbon atoms, 2 to 100 carbon atoms or 2 to 20 carbon atoms. Examples of R include linear aliphatic groups such as n-alkyl bridges having 1 to 10,000 carbon atoms, such as 2 to 20 carbon atoms or 2 to 6 carbon atoms. Further examples of R include polymer linker groups, DNA groups and peptide groups; example peptides include the use of a cysteine residue in a peptide linker, which can be functionalized with maleimide reagents; furthermore, the natural amine and carboxylic groups of a peptide's N- and P-termini may function to form the amide linking $X^1$ and $X^2$ groups when attached to the dye and QD.

The sensing agents of the present disclosure can be formed by any suitable method. For example, a dye compound can be attached to the quantum dot by a reaction process that forms any of the coupling moieties discussed above. One suitable reaction process is shown in Example 1 for forming a sensing agent from a carboxy derivatized Rhodamine B dye, a quantum dot passivated with a carboxy group and an amine terminated disulfide bridge containing linker molecule. The carboxy groups on the QD and the Rhodamine B dye form amide anchor groups with the amine groups of the linker, thereby forming a disulfide containing coupling moiety as shown in the final QD/Dye product, as illustrated in the Example 1 mechanism. A similar mechanism may be used where the Rhodamine B dye and quantum dots are functionalized with amine groups instead of the carboxy groups of Example 1, and the linker molecule is terminated with carboxy groups instead of amine groups, where the amine and carboxy groups react to form amide coupling moieties. In methods where the QD is coated, the coating can optionally include the amine or carboxy groups, or other groups for anchoring the linker molecule. One of ordinary skill in the art would be able to determine a variety of other mechanisms for forming the sensing agents of the present disclosure.

Figure 3:
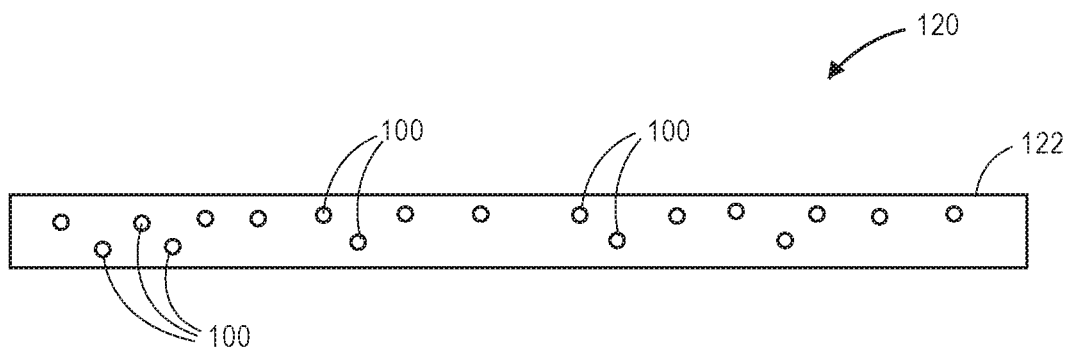
FIG. 3 illustrates an example of a ratiometric sensor, according to an embodiment of the present disclosure.

The present disclosure is also directed to a sensor for detection of hydrogen sulfide or disulfide. In an embodiment, the sensor can be a ratiometric sensor that employs any of the sensing agents that provide a ratiometric response described herein. Any of the sensors described herein, such as that of FIG. 3, can be ratiometric. Referring to FIG. 3, the sensor 120 comprises a support matrix 122 and a sensing agent 100 embedded in the support matrix 122. The sensing agent 100 comprises a quantum dot and a dye moiety coupled to the quantum dot, as described herein. Any of the sensing agents described herein that are capable of sensing, such as by exhibiting a ratiometric response to, at least one species chosen from hydrogen sulfide and bisulfide, can be employed for use in any of the sensors of the present disclosure.

The sensors of the present disclosure can be selective towards at least one analyte chosen from bisulfide and hydrogen sulfide, when compared to other compounds, such as other thiols. For example, the sensors can be selective to bisulfide ($HS^-$ anion) compared to other thiols chosen from glutathione and cysteine.

The sensors can have a suitable detection limit that allows for detection at relatively low concentrations of at least one analyte selected from hydrogen sulfide and bisulfide. In an example, the sensors of the present disclosure have a detection limit for bisulfide, in water, of less than 2 µM at a sensor concentration of $3.4 \times 10^{-9}$ M as determined by the boot strap method, where the conjugated dye:QD ratio is 1.3:1. The detection limit may be lower for sensing $H_2S$, especially when embedded in a solid matrix and employing a focused $H_2S$ stream. For example, detection limits for $H_2S$ may range down to 1 ppb, or lower, such as 1 ppt (part per trillion). Thus, the sensors may also be capable sensing hydrogen sulfide in breath.

The matrix support 122 of the sensor can comprise any suitable material or combination of materials that provides the desired support and that is compatible with the functionality of the sensor. The matrix can itself be sufficiently solid so as to provide the desired support. Alternatively, the matrix support 122 can comprise a matrix, in the form of a resin, gel or other solid, semi-solid or liquid material, coated on a substrate that provides the desired support. As examples, the material for the support matrix can be chosen from paper, a polymer, such as polydimethylsiloxane (PDMS), and a combination thereof.

EXAMPLES

Example 1A

Bisulfide-Reactive Carboxyrhodamine B Synthesis

The bisulfide-reactive rhodamine B derivative used in this study was synthesized following the outline in Scheme 1, and the discussion below.

Synthesis of Carboxyrhodamine B (Compound 3): A mixture of 3-diethyl aminophenol (Compound 1) (1.03 g, 6.05 mmol), and 1,2,4-benzenetricarboxylic anhydride (Compound 2) (0.6 g, 3.02 mmol) was heated to 195° C. in the presence of a catalytic amount of $ZnCl_2$ under a nitrogen atmosphere for 1 h. The resulting red mixture was cooled to room temperature, and dissolved in 5% NaOH solution. The mixed isomers of carboxyrhodamine B were precipitated out of the solution by acidification using HCl (pH=1). 5- and 6-carboxyrhodamine B (Compound 4) isomers were separated as TEA salts by flash chromatography (DCM:MeOH:TEA 4:1:0.5) according to the methods outlined in Brunet, A.; Aslam, T.; Bradley, M. *Bioorg. Mid. Chem. Lett.* 2014, 24, 3186-3188. Solvents were evaporated under reduced pressure. Each isomer was dissolved in ETOAc (40 mL), and washed with 1M $KHSO_4$ (3×30 mL), brine (30 mL), and dried over anhydrous $Na_2SO_4$ to obtain pure 5-carboxyrhodamine B (575 mg, 39%), and 6-carboxyrhodamine B (452 mg, 30%).

Synthesis of 6-Carboxytetraethylrhodamine N-Hydroxysuccinimide ester (Compound 6): 6-carboxyrhodamine B (Compound 5) (100 mg, 0.2 mmol), DMAP (122 mg, 1 mmol), and TEA (140 μL, 1 mmol) were dissolved in dry DCM (10 mL). DSC (105 mg, 0.4 mmol) was added, and the mixture was stirred under nitrogen atmosphere at room temperature for 1 h. After 1 h the reaction was quenched by addition of AcOH (120 μL, 2 mmol), and the final product was purified by flash chromatography using 1% AcOH in acetone followed by MeOH:DCM:AcOH (9:89:2) as eluent (65% yield).

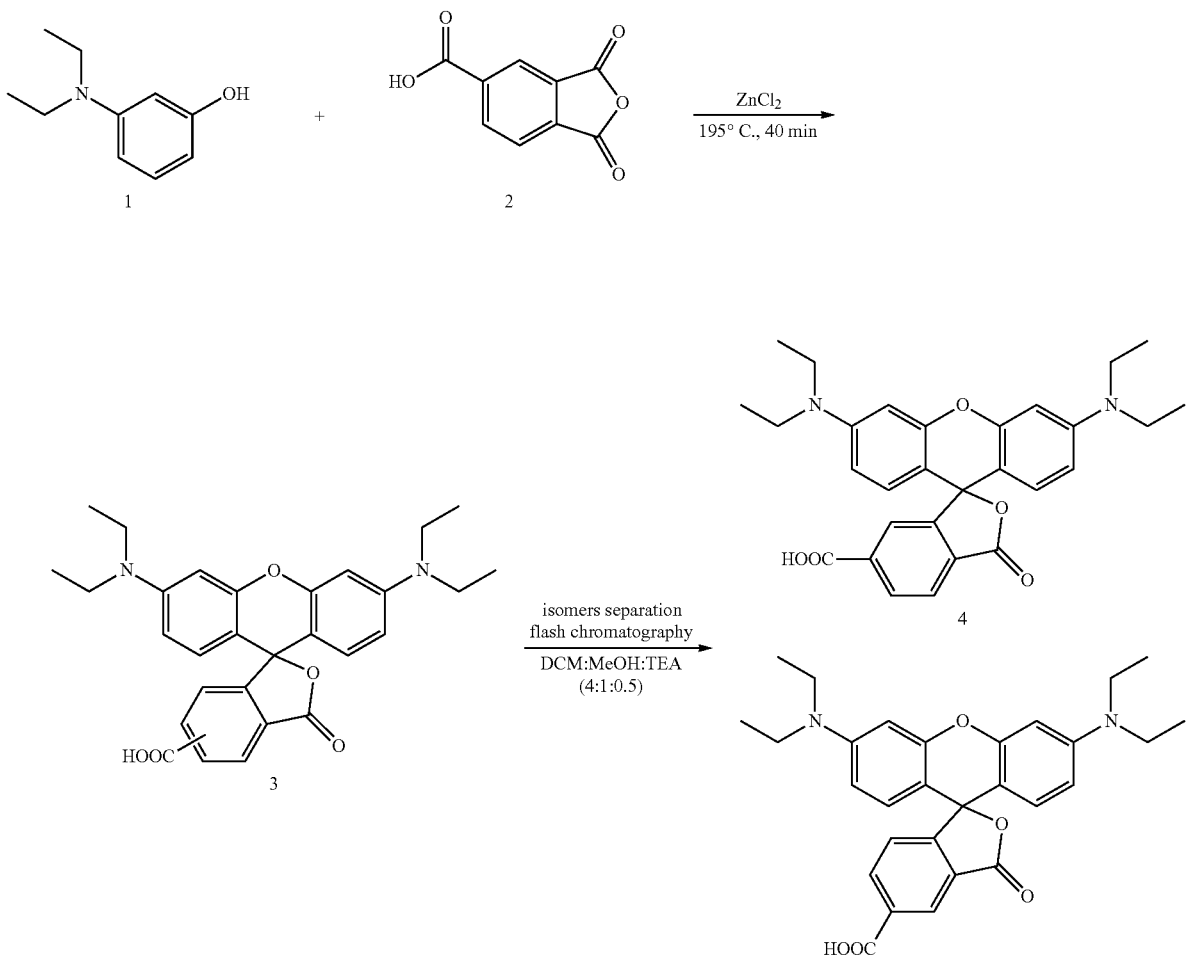

-continued
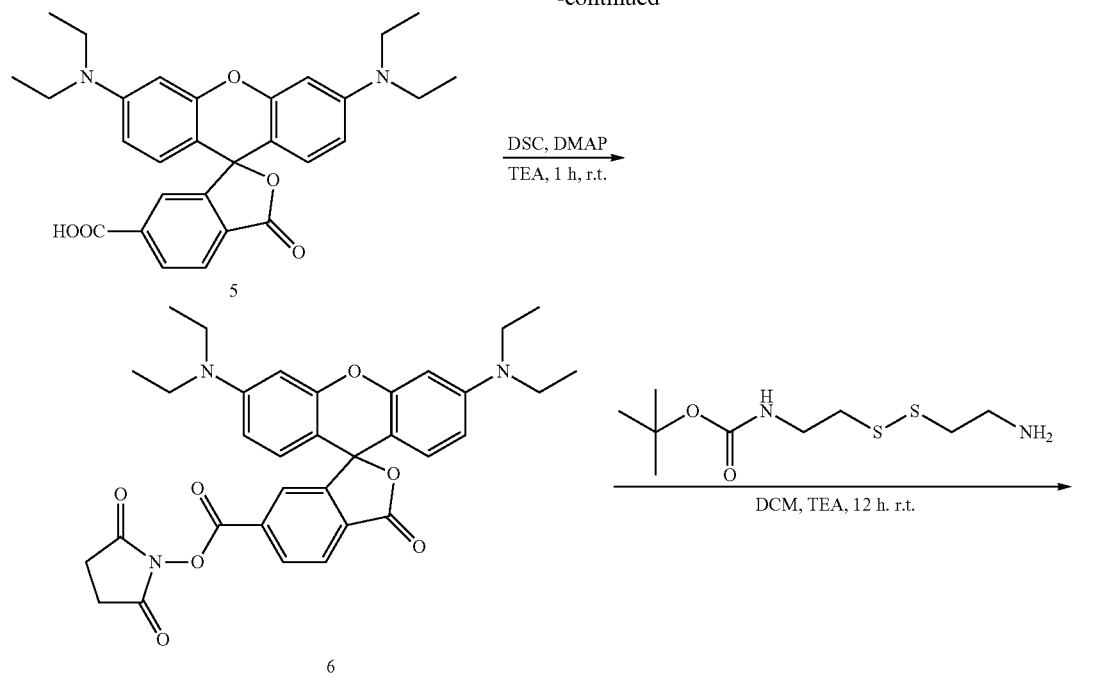
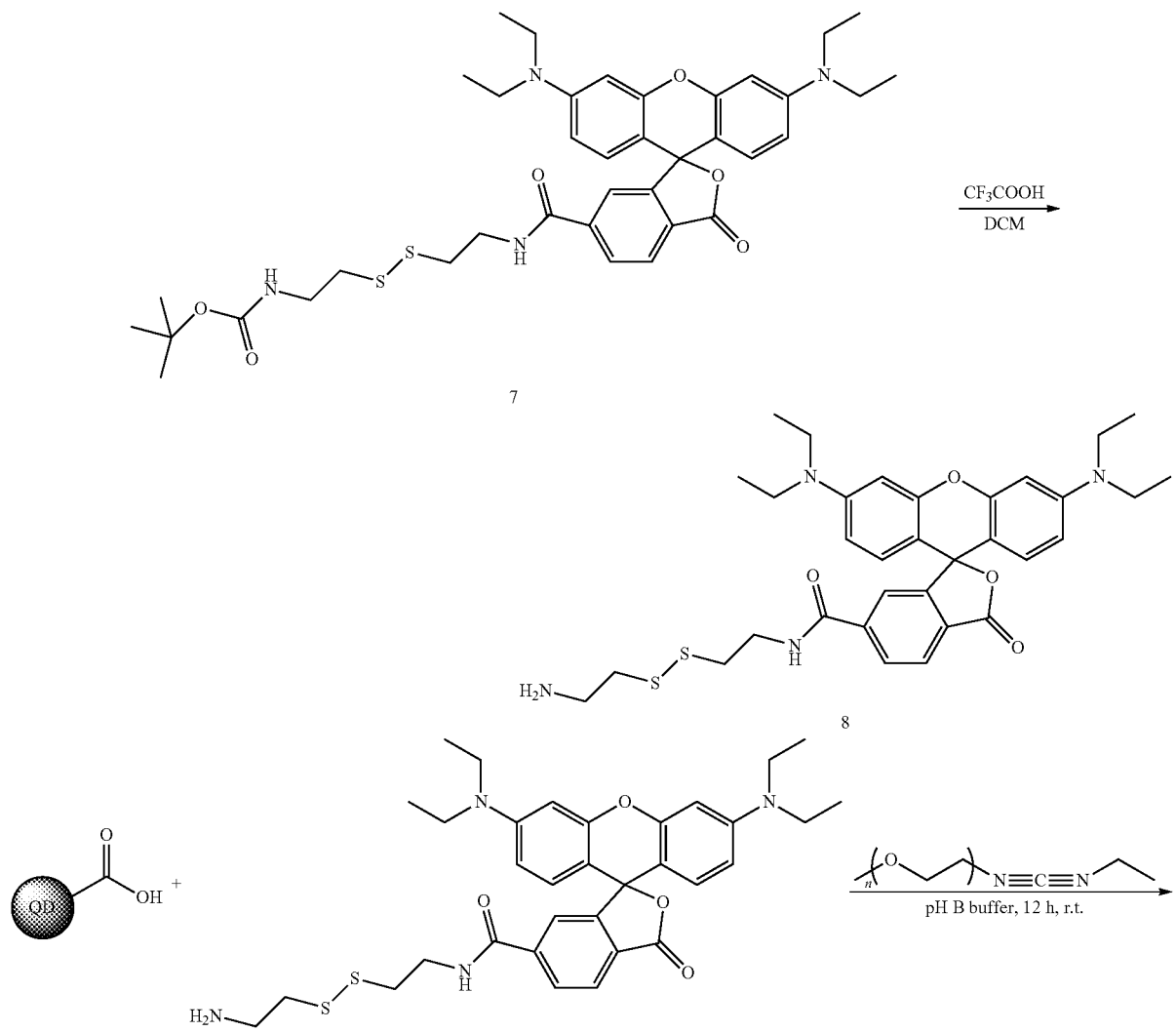

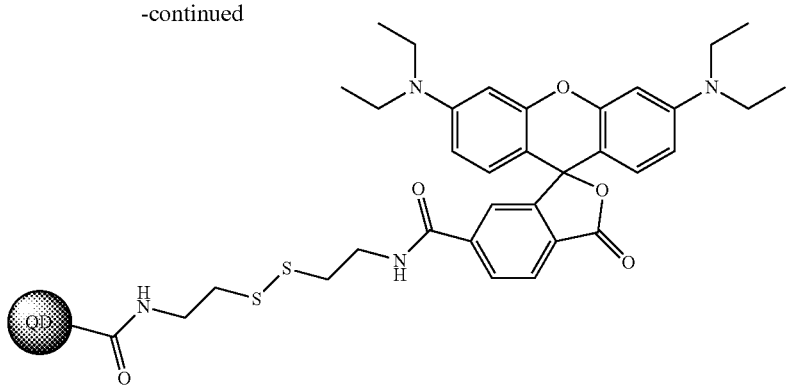

Synthesis of N-(2((2-aminoethyl)disulfanyl)ethyl)-3',6'-bis(diethylamino)-3-oxo-3H-spiro [isobenzofran-1,9'-xanthene]-6-carboxamide (Compound 8): 6-carboxytetraethyl-rhodamine N-hydroxysuccinimide ester (Compound 6) (58.4 mg, 0.1 mmol), mono-t-boc-cystamineHCl (28.81 mg, 0.1 mmol), and TEA (14 μL, 0.1 mmol) were dissolved in dry DCM, and stirred under nitrogen atmosphere at room temperature overnight. The next day the solvent was evaporated under reduced pressure, and the resulting residue was purified by flash chromatography (DCM:MeOH 85:15) to obtain compound 7. For boc deprotection, the resulting compound was dissolved in DCM (4 mL), and then CF$_3$COOH (2 mL) was added. After the mixture was stirred for 2 h under nitrogen atmosphere at room temperature, the solvent was evaporated under reduced pressure. The product was purified by flash chromatography (DCM:MeOH:TEA 4:1:0.5) to obtain compound 8 (81% yield).

Example 1B

QDs Synthesis, PVC Modification, and Water Solubilization

CdSe/CdZnS core/shell QDs were synthesized according to previously published protocols. Approximately 0.5 g of the crude sample was processed by addition of a small amount of isopropanol followed by methanol to induce flocculation. The supernatant was discarded, and the precipitate was dried under vacuum. The QDs were dissolved in 2 mL of THF, and 50 μL of a PVC coating solution (50 mg high molecular weight polyvinyl chloride and 100 mg of bis(2-ethylhexyl) sebacate dissolved in 5 mL of THF) was added. The mixture was stirred gently overnight, after which the solvent was evaporated under reduced pressure. Next, 65 mg of 40% octylamine-modified PAA was added to the QDs followed by ~3 mL of dry THF. The solution was sonicated for several minutes to dissolve the polymer completely. The solvent was evaporated under reduced pressure, and 0.1 M NaOH solution was added to disperse the plastic coated QDs into water. The solution was dialyzed to neutrality to remove excess polymer. The solution was then filtered through a 0.2 μm syringe filter to yield a monodisperse plastic-coated water-soluble QD solution. Samples without PVC modification were prepared by repeating the procedure above without the addition of the PVC coating solution.

Example 1C

Compound 8 Dye Conjugation to QDs

A solution of ~5 mg of MPEG 350 CD dissolved in 0.5 mL of water-solubilized CdSe/CdZnS QDs (1.24×10$^{-6}$ M) was stirred for 30 min. The QDs were made as described in Example 1B. Next, a sub-milligram quantity of compound 8 (Example 1A) was dissolved in pH 8 phosphate buffer and was added dropwise to the activated QD solution until the dye emission appeared to slightly dominate the dots under illumination with a black light. Next, 2 mL of pH 8 phosphate buffer was added, and the reaction was allowed to stir overnight. The next day, dialysis was performed using centrifugation filters to remove excess unreacted dye. The QD sulfide sensor solution was then diluted to working concentration of 3.43×10$^{-8}$ M using pH 7.4 Tris-HCl buffer. The conjugation yield was calculated to be 42% by comparing absorbance spectra before and after dialysis, and the number of the dye per QD was determined to be 1.3 based on the absorptivity of the dye component.

Example 1D

QD/Bisulfide-Reactive Carboxyrhodamine Dye (Compound 8) Sensor

The sensing agent of Example 1C was diluted into a buffer solution (1 mL) to the working concentration of 3.4×10$^{-8}$ M. The solution was held in a 1 mL quartz curvette (itself having standard 1 cm×1 cm dimensions) and placed into the optical cavity of a fluorometer. Emission of the sensor was recorded in the buffer solution alone, followed by measurements with H$_2$S as a sulfide source added to the buffer, as described in Example 2 below.

Example 2

Figure 4A:
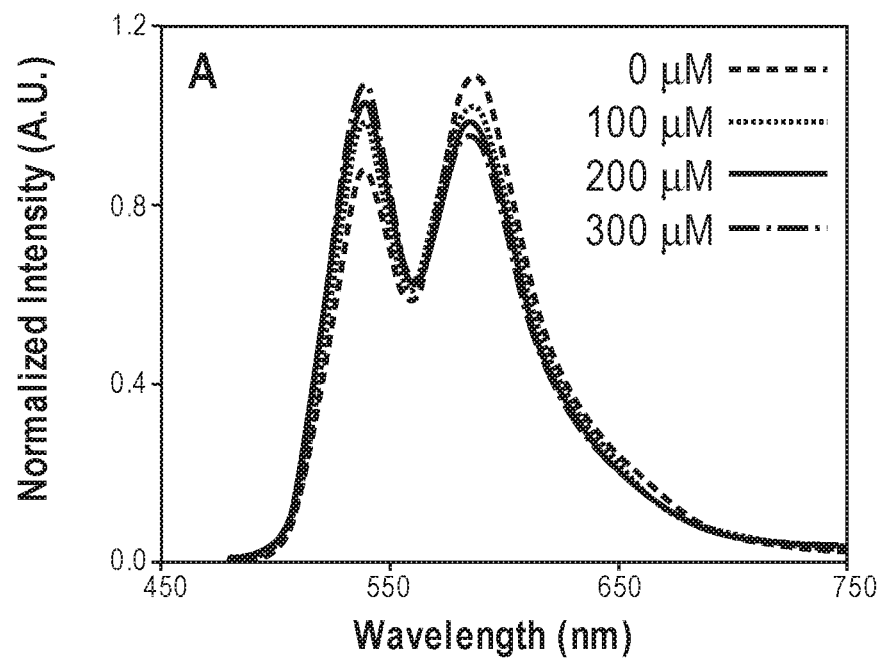
FIG. 4A is a graph that shows normalized emission of the coupled QD/bisulfide-reactive carboxyrhodamine dye (compound 8) sensor at a sensor concentration of $3.4 \times 10^{-8}$ M upon exposure to HS$^-$, according to an example of the present disclosure.

The sensing agent of Example 1C was tested using the setup as described in Example 1D using freshly-prepared sodium sulfide in pH 7.4 Tris-HCl buffer solution to represent an H$_2$S source. FIG. 4A shows normalized emission of the coupled QD/bisulfide-reactive carboxyrhodamine dye (compound 8) sensor of Example 1 at a sensor concentration of about 3.4×10$^{-8}$ M upon exposure to HS$^-$. The fluorescent response of the sensor shown in FIG. 4A was quantified by fitting multiple Gaussian functions to the sulfide-dependent emission spectra to separate the QD and dye components. The integrated emission ratio of the QD donor:dye acceptor was plotted as a function of the HS$^-$ concentration (FIG. 4B and Table 1), which shows a linear correlation. The detection limit was determined to be 21.6±0.4 μM using the boot strap method, as described by Efron, B. *Ann. Statist.,* 1979, 7, 1-26. Note that the detection limit of ratiometric sensors is scalable with concentration to within reasonable limits as determined by the detection efficiency. As such, the sensor was diluted by ×10, reanalyzed, and, was found to have a detection limit of 1.36±0.03 µM using the data shown in FIG. 5 and in Table 2. FIG. 5A shows normalized emission of the diluted sensor upon exposure to HS⁻, according to an example of the present disclosure, FIG. 5B shows calibration data from the ratio of the integrated emission of the QD donor over the dye acceptor as a function of HS⁻ concentration reveals a detection limit of 1.36±0.03 µM at a sensor concentration of $3.4 \times 10^{-9}$ M.

TABLE 1

Figure 4B:
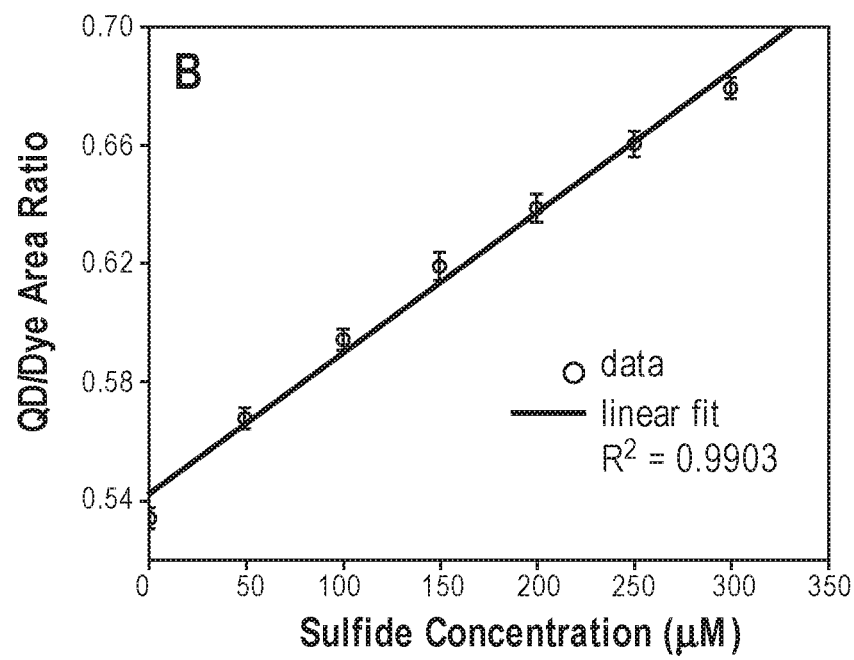
FIG. 4B is a graph that shows the ratio of the integrated emission of the QD donor over the dye acceptor as a function of concentration, according to an example of the present disclosure.
Figures 5A, 5B:
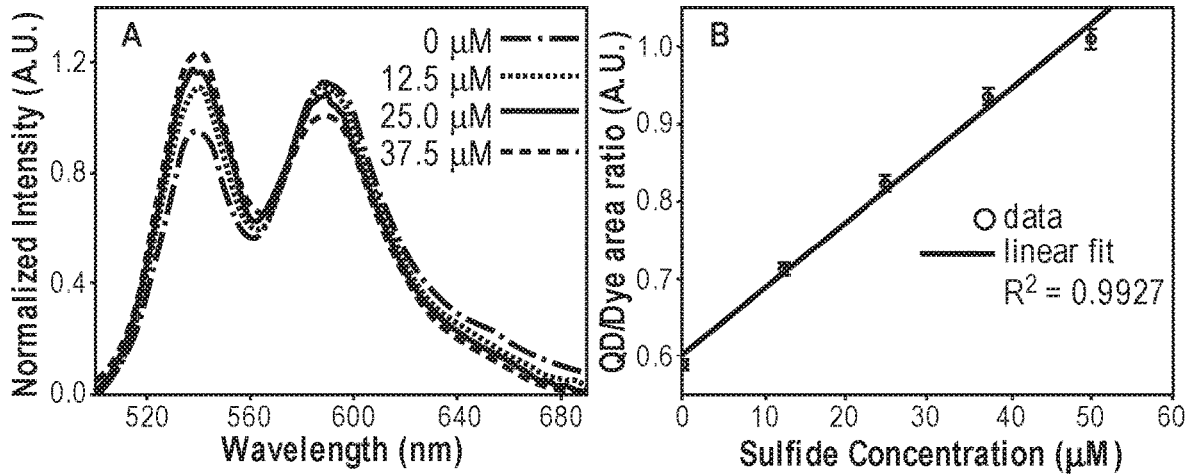
FIG. 5A is a graph that shows the normalized emission of the diluted sensor upon exposure to HS$^-$, according to an example of the present disclosure.
FIG. 5B is a graph that shows calibration data from the ratio of the integrated emission of the QD donor over the dye acceptor as a function of HS$^-$ concentration, which reveals a detection limit of $1.36 \pm 0.03$ µM at a sensor concentration of $3.4 \times 10^{-9}$ M, according to an example of the present disclosure.

Ratio of the integrated emission of the QD donor over the dye acceptor shown in FIG. 4B as a function of HS⁻ concentration.

| HS⁻ Conc (µM) | QD/Dye | STD |
|---|---|---|
| 0 | 0.5344 | 0.003415 |
| 50 | 0.5679 | 0.003625 |
| 100 | 0.5945 | 0.004075 |
| 150 | 0.6192 | 0.00475 |
| 200 | 0.6389 | 0.004954 |
| 250 | 0.6607 | 0.004088 |
| 300 | 0.6792 | 0.003734 |

TABLE 2

Ratio of the integrated emission of the QD donor over the dye acceptor shown in FIG. 5B as a function of HS⁻ concentration.

| HS⁻ Conc (µM) | QD/Dye | STD |
|---|---|---|
| 0 | 0.587236 | 0.0075 |
| 12.5 | 0.71225 | 0.0075 |
| 25 | 0.823432 | 0.0095 |
| 37.5 | 0.93562 | 0.01 |
| 50 | 1.00928 | 0.0125 |

The data in FIGS. 1 and 2 demonstrate that the QD/bisulfide-reactive carboxyrhodamine dye has a linear response in bisulfide concentration down to 1.36 uM.

Example 3

Selectivity

Figure 6:
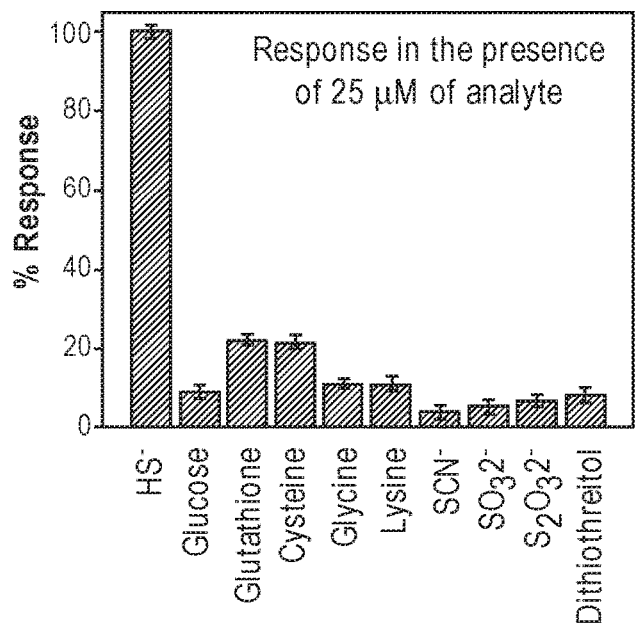
FIG. 6 is a graph that shows the fluorescence intensity ratio change in response to various relevant analytes (25 µM), where the data is being normalized against the response to bisulfide, according to an example of the present disclosure.

To study the selectivity, the ratiometric response of the QD-dye complex was measured after exposure to various biological thiols and amino acids in pH 7.4 Tris-HCl buffer (FIG. 6 and Table 3). FIG. 6 shows fluorescence intensity ratio change in response to various relevant analytes (25 µM), where data being normalized against the response to bisulfide. As can be seen, the sensor has a stronger response towards the HS⁻ anion compared to other thiols (glutathione and cysteine), which is believed to be a result of the smaller size and greater nucleophilicity of the analyte. Thus, the response is specific to bisulfide and/or $H_2S$ and not to other sulfur containing small molecules.

TABLE 3

Fluorescence intensity ratio change in response to various relevant analytes (25 µM). The data (also shown in FIG. 5) are normalized against the response to bisulfide.

| | % Response | STD |
|---|---|---|
| $H_2S$ | 100 | 1.49 |
| Glucose | 9.09 | 1.73 |
| Glutathion | 22.2 | 1.16 |

TABLE 3-continued

Fluorescence intensity ratio change in response to various relevant analytes (25 µM). The data (also shown in FIG. 5) are normalized against the response to bisulfide.

| | % Response | STD |
|---|---|---|
| Cysteine | 21.43 | 1.74 |
| Glycine | 11 | 1.22 |
| Lysine | 10.91 | 1.83 |
| NaSCN | 3.98 | 1.51 |
| $Na_2SO_3$ | 5.2 | 1.62 |
| $Na_2S_2O_3$ | 6.56 | 1.27 |
| DTT | 7.99 | 1.9 |

Example 4

Sensing Agent without Linker

Figure 7A:
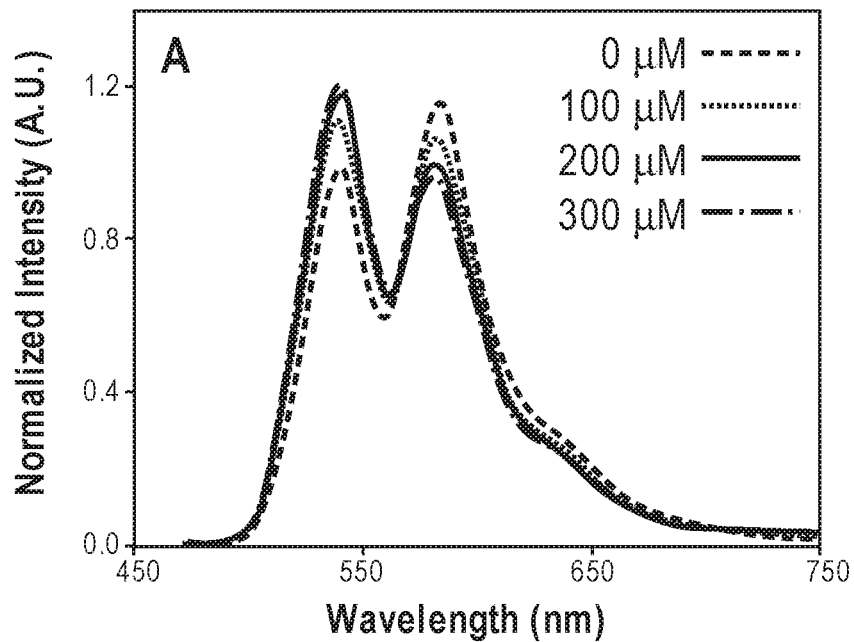
FIG. 7A is a graph that shows the emission spectra of the QD/rhodamine B piperazine conjugated chromophore in the presence of increasing concentrations of Na$_2$S, according to an example of the present disclosure.
Figure 7B:
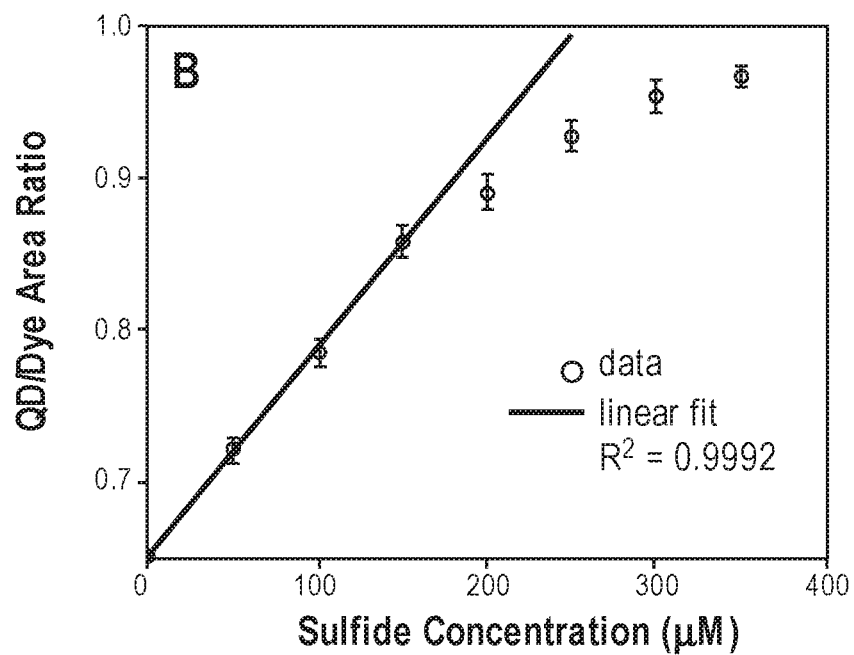
FIG. 7B is a graph that shows calibration data from the ratio of the integrated emission of the QD donor over the dye acceptor as a function of HS$^-$ concentration, which reveal a roll-off of the response at higher levels of bisulfide that is not observed in the QD/bisulfide-reactive carboxyrhodamine dye conjugate, according to an example of the present disclosure.

A sensing agent and sensor were made in which a Rhodamine B derivative was used as the organic chromophore. In particular, the sensing agent was an amide bond-coupled (and thus non-sulfide cleavable) QD/Rhodamine B piperazine chromophore. The sensor responded to bisulfide ion in a similar manner to that observed in the QD/bisulfide-reactive dye system (see FIG. 7 and Table 4). In particular, FIG. 7A shows the emission spectra of QD/rhodamine B piperazine conjugated chromophore in the presence of increasing concentrations of $Na_2S$. FIG. 7B shows calibration data from the ratio of the integrated emission of the QD donor over the dye acceptor as a function of HS concentration reveal a roll-off of the response at higher levels of bisulfide that is not observed in the QD/bisulfide-reactive carboxyrhodamine dye conjugate. The response shows a linear correlation between the integrated QD:dye emissions ratio versus HS⁻ concentration to 150 µM of bisulfide under the conditions employed. However, the response saturated above this range, which was not true for the reduction-sensitive FRET system of Example 1, as discussed above. This is likely due to the difference in analyte recognition mechanisms; regardless, the amide-bonded coupled chromophore was not further studied due to this limitation. Thus the sulfide cleavable linkage makes the QD/bisulfide-reactive carboxyrhodamine dye a superior system for sensing bisulfide across a wide concentration range.

TABLE 4

Ratio of the integrated emission of the QD donor over the dye acceptor shown in FIG. 7B as a function of HS⁻ concentration.

| HS⁻ Conc (µM) | QD/Dye | STD |
|---|---|---|
| 0 | 0.6522 | 0.0034 |
| 50 | 0.7211 | 0.0085 |
| 100 | 0.7848 | 0.0089 |
| 150 | 0.8589 | 0.0111 |
| 200 | 0.8909 | 0.0125 |
| 250 | 0.9273 | 0.0107 |
| 300 | 0.9533 | 0.0101 |
| 350 | 0.9672 | 0.007 |

Example 5

Sensing Agent with Coated Quantum Dot

Figure 8A:
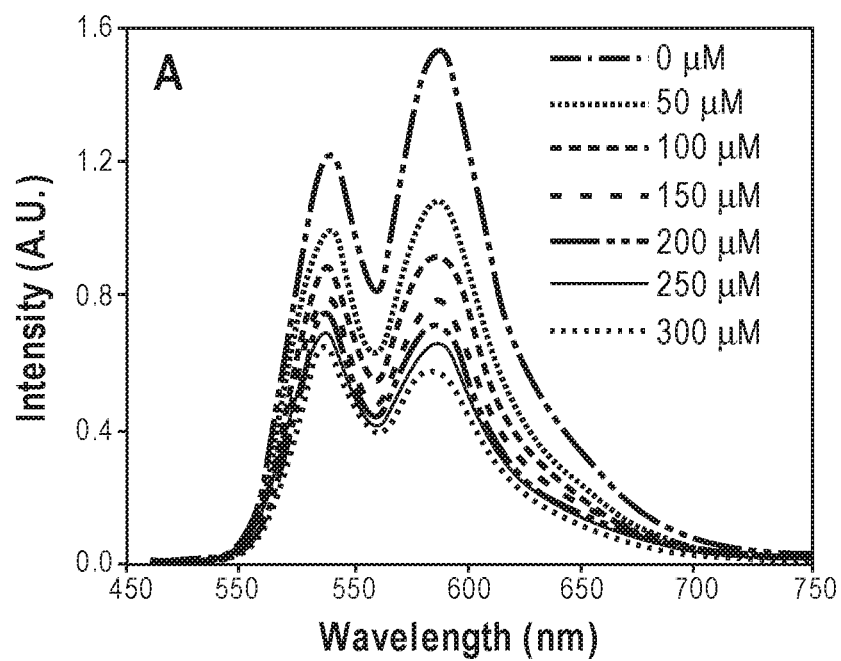
FIG. 8A is a graph that shows the raw emission spectra of the QD/sulfide reactive dye coupled chromophore, the normalized data from which appear in FIG. 4A, according to an example of the present disclosure.
Figure 8B:
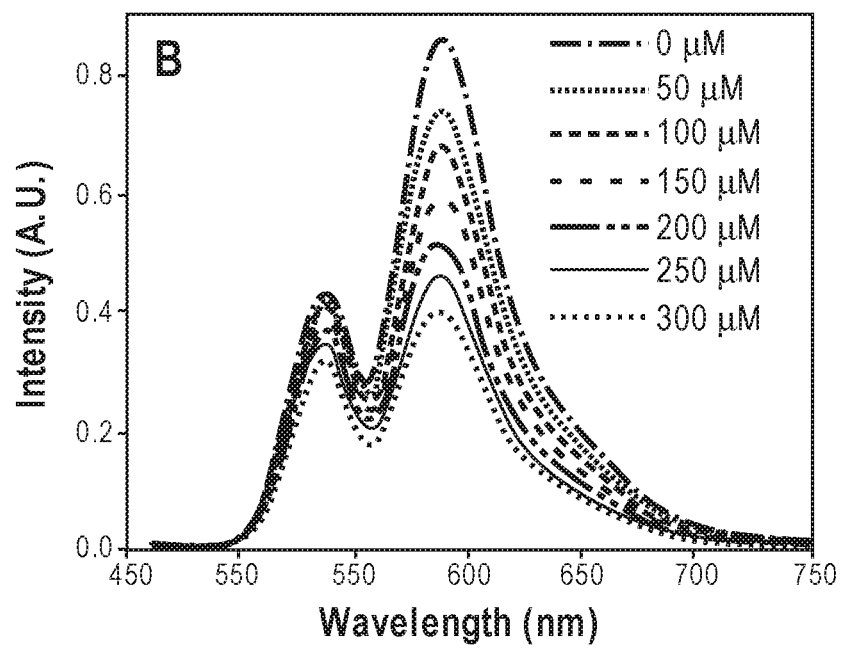
FIG. 8B is a graph that shows the raw emission spectra for a PVC-modified. ("plastic coated") QD/sulfide reactive dye in the presence of increasing concentrations of Na$_2$S, according to an example of the present disclosure. The data show that the quantum dot emission is less perturbed in the plastic coated sample.
Figure 9A:
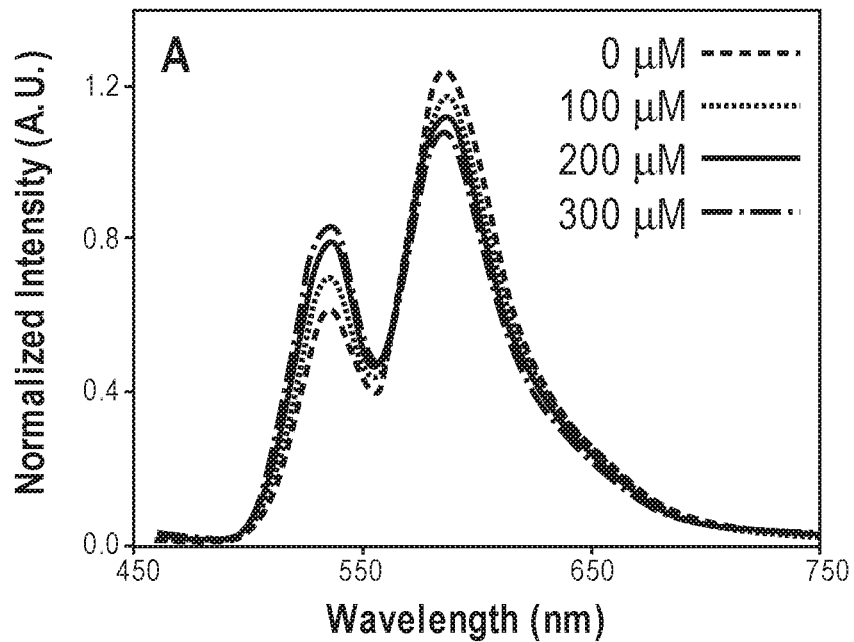
FIG. 9A is a graph that shows the normalized emission of the PVC-coated QD/bisulfide reactive dye sensor ($3.4 \times 10^{-8}$ M) upon exposure to HS$^-$ (raw data appear in FIG. 8B), according to an example of the present disclosure.
Figure 9B:
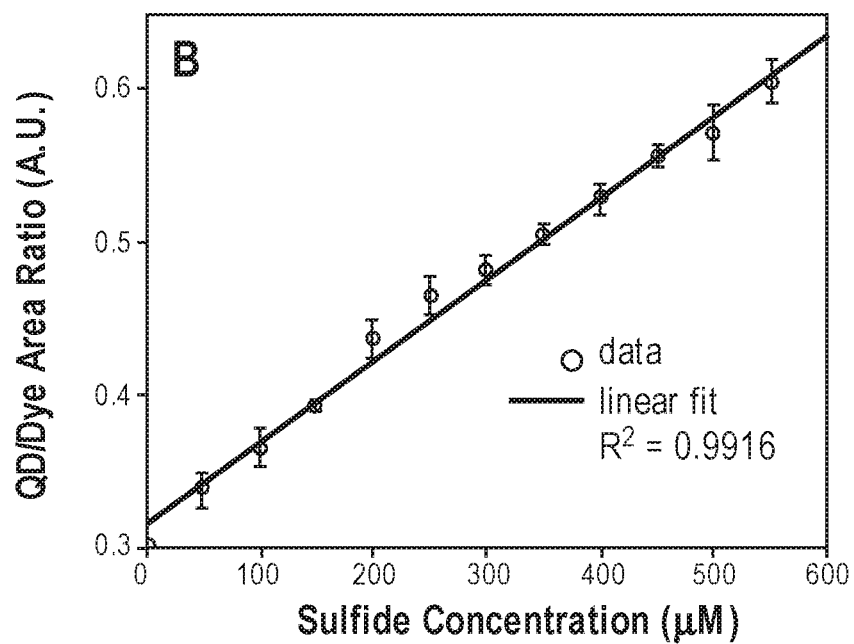
FIG. 9B is a graph that shows a ratio of the integrated emission of the QD donor over the dye acceptor as a function of HS$^-$ concentration, according to an example of the present disclosure. The detection limit was determined to be $41.9 \pm 0.3$ µM for a QD sensor concentration of $3.4 \times 10^{-8}$ M.
Figure 10A:
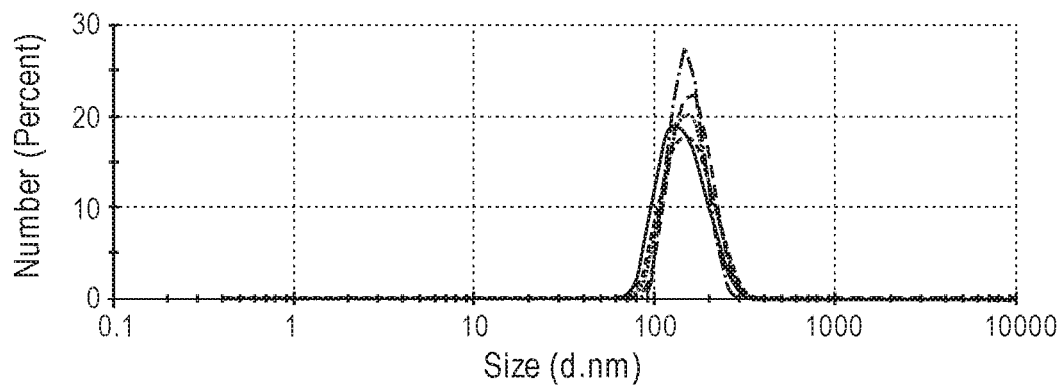
FIG. 10A is a graph that shows the DLS for coated QD as a function of percent population vs. diameter, according to an example of the present disclosure.
Figure 10B:
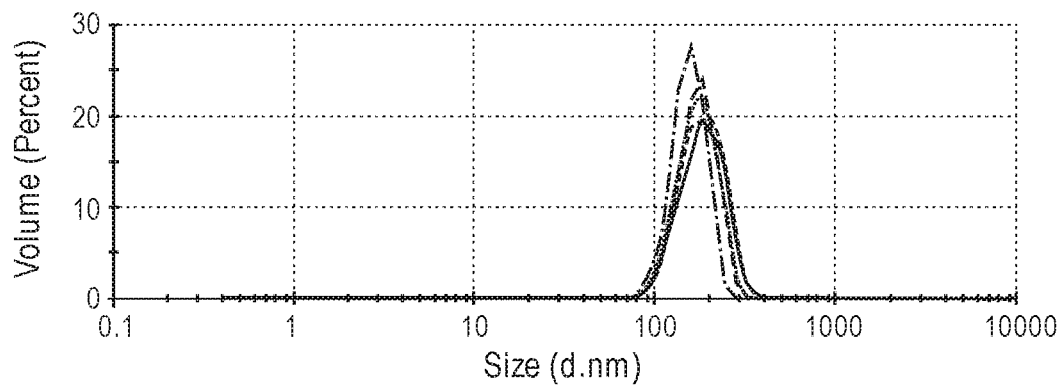
FIG. 10B is a graph that shows the DLS for coated QDs as a function of volume population versus diameter, according to an example of the present disclosure.
Figure 10C:
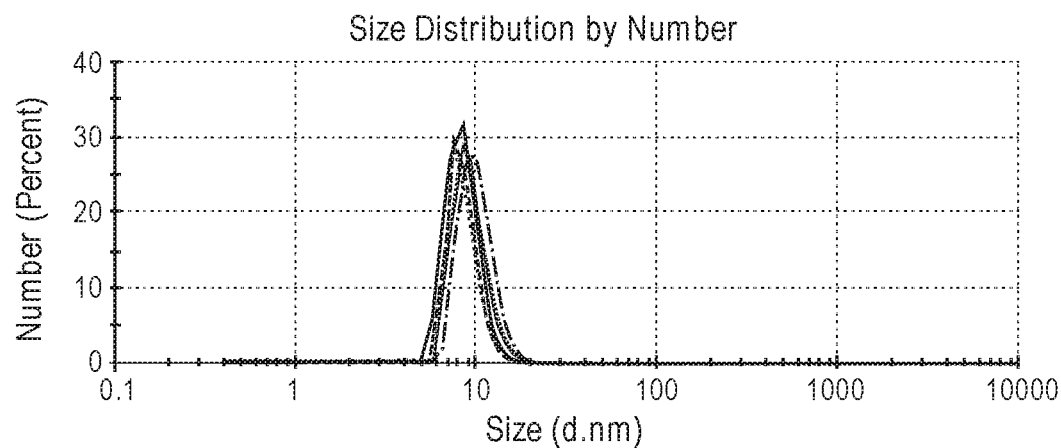
FIG. 10C is a graph that shows the DLS for uncoated QD as a function of percent population vs. diameter, according to an example of the present disclosure.
Figure 10D:
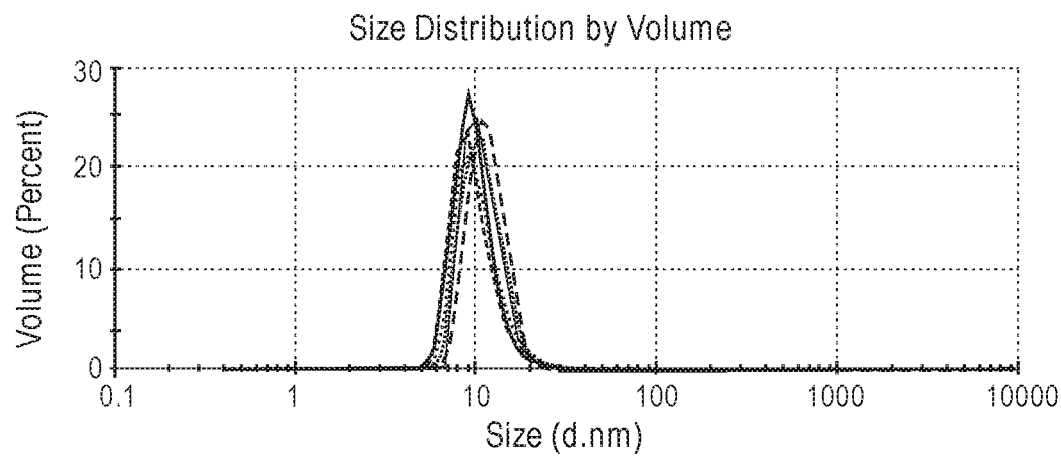
FIG. 10D is a graph that shows the DLS for uncoated QDs as a function of volume population versus diameter, according to an example of the present disclosure. The data show that the PVC-modified QDs of FIGS. 10A and 10B are significantly larger than the unmodified QD samples of FIGS. 10C and 10D in water.

While FIG. 4A shows that the emission of the QD/bisulfide-reactive carboxyrhodamine B dye with a disulfide bond linker has a clean response to bisulfide exposure with a clear isosbestic point appearing at 570 nm, the absolute intensity of the sensor's emission was reduced as seen in the unnormalized spectra in FIG. 8A. In particular, FIG. 8A shows raw emission spectra of QD/sulfide reactive dye coupled chromophore, the normalized data from which appear in FIG. 4A. It was determined that the overall loss of fluorescence efficiency was due to bisulfide quenching of the QD donor component. As such, several avenues were explored to protect the QD from quenching by the analyte, one of which was to coat the QDs with polyvinyl chloride (PVC) before water solubilization with 40% octylamine-modified poly (acrylic acid). These water soluble, "plastic-coated" QDs were conjugated to the bisulfide-reactive carboxyrhodamine B dye and were then titrated with bisulfide solution. FIG. 8B shows unnormalized, raw emission spectra for a PVC-modified ("plastic coated") QD/sulfide reactive dye in the presence of increasing concentrations of $Na_2S$. The data show that the quantum dot emission is less perturbed in the plastic coated sample. The normalized emission and linear response of this sensor are shown in FIG. 9 and Table 5, where it can be see that the plastic coating reduced quenching of the QDs due to $HS^-$ exposure. In particular, FIG. 9A shows normalized emission of the PVC-coated QD/bisulfide reactive dye sensor ($3.4 \times 10^{-8}$ M) upon exposure to $HS^-$ (raw data appear in FIG. 8B). FIG. 9B shows a ratio of the integrated emission of the QD donor over the dye acceptor as a function of $HS^-$ concentration. The detection limit was determined to be $41.9 \pm 0.3$ μM for a QD sensor concentration of $3.4 \times 10^{-8}$ M. The ratiometric response to bisulfide was linear with a detection limit of $41.9 \pm 0.3$ μM; in fact these data appear nearly identical to that shown for the sensing agents of Example 1 in FIG. 4.

TABLE 5

Ratio of the integrated emission of the QD donor over the dye acceptor shown in FIG. 9B as a function of $HS^-$ concentration

| $HS^-$ Conc (μM) | QD/Dye | STD |
|---|---|---|
| 0 | 0.3036 | 0.016969 |
| 50 | 0.339 | 0.01246 |
| 100 | 0.3664 | 0.01442 |
| 150 | 0.3932 | 0.00465 |
| 200 | 0.4385 | 0.012899 |
| 250 | 0.4662 | 0.01449 |
| 300 | 0.4817 | 0.009755 |
| 350 | 0.5058 | 0.007041 |
| 400 | 0.529 | 0.0105 |
| 450 | 0.5568 | 0.008097 |
| 500 | 0.5729 | 0.0195 |
| 550 | 0.6057 | 0.016 |

Dynamic Light Scattering (DLS) results shown in FIG. 10 reveal that the plastic-coated. QDs are ~150 nm in diameter (FIGS. 10A and 10B) which is a significant increase from ~8.5 nm observed in un-modified water-soluble dots (FIGS. 10C and 10D). Furthermore, these dots did not diffuse freely and distribute themselves evenly in live cells after microinjection, most likely due to their large size. While this may pose a limitation for the plastic coated quantum dots in sensing bisulfide concentration in a cell this system may still be ideal other sensing applications, such as the sensing of hydrogen sulfide in breath.

What is claimed is:

1. A sensor, comprising:
   a support matrix; and
   a sensing agent embedded in the support matrix, the sensing agent comprising:
   a quantum dot; and
   a dye moiety coupled to the quantum dot,
   wherein the sensing agent is capable of sensing at least one analyte chosen from hydrogen sulfide by FRET modulation between the quantum dot and the dye moiety, and wherein the sensing agent has the formula

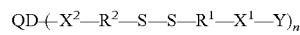

wherein:
   QD is the quantum dot,
   Y is the dye moiety,
   wherein the dye moiety is a rhodamine group selected from one of:

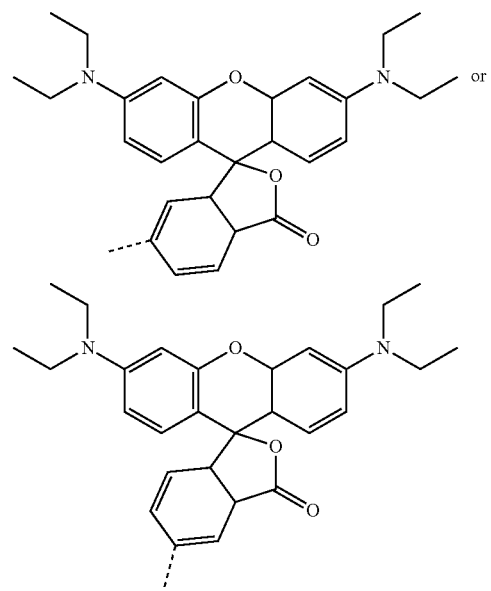

where the dotted bond shows the position of attachment to the coupling moiety;
   $R^1$ and $R^2$ organic bridging groups that will, in combination with the associated linkages $X^1$ and $X^2$ and disulfide bond (—S—S—), provide a distance between the dye and the QD that is from about 0.1 nm to about 10 nm, and
   $X^1$ and $X^2$ are linkages that respectively function to attach the $R^1$ group to the dye and $R^2$ group to the quantum dot;
   n is the number of coupling-dye groups attached to the QD;
   wherein $R^1$ and $R^2$ are alkyl bridges and $X^1$ and $X^2$ are amide linkages; and
   wherein the sensor has a detection limit for bisulfide, in water, of less than 2 μM at a sensor concentration of $3.4 \times 10^{-9}$ M as determined by the boot strap method, where the conjugated dye:QD ratio is 1.3:1.

2. The sensor of claim 1, wherein the sensing agent is capable of exhibiting a ratiometric response to at least one analyte chosen from hydrogen sulfide ($H_2S$) and bisulfide.

3. The sensor of claim 1, wherein the support matrix is chosen from paper, a polymer and a combination thereof.

4. The sensor of claim 1, wherein the dye moiety is coupled to the quantum dot via a disulfide bridge coupling moiety that is cleavable by the at least one analyte.

5. The sensor of claim 1, wherein the quantum dot comprises an emissive material selected from ZnS, ZnSe, ZnSe/ZnS, CdS, CdS/ZnS, CdZnS, CdZnS/ZnS, CdSe, CdZnSe, CdSeS, CdZnSeS, CdSe/ZnS, CdZnSe/ZnS, CdSeS/ZnS, CdZnSeS/ZnS, CdSe/CdZnS, CdZnSe/CdZnS, CdSeS/CdZnS, CdZnSeS/CdZnS, CdTe, CdSeTe, CdTe/ZnS, CdSeTe/ZnS, CdTe/CdZnS, CdSeTe/CdZnS, CdTe/ZnSe, CdSeTe/ZnSe, CdTe/ZnSeS, CdSeTe/ZnSeS, ZnSe/CdS, CdS/ZnSe, ZnSe/CdS/ZnS, CdS/ZnSe/ZnS, CdSe/CdTe, CdTe/CdSe, CdSe/CdTe/ZnS, CdTe/CdSe/ZnS, CdSe/CdTe/ZnSe, CdTe/CdSe/ZnSe, $AgInS_2$, $AgInS_2$/ZnS, $CuInS_2$, $CuInS_2$/ZnS, $AgInSe_2$, $AgInSe_2$/ZnS, $CuInSe_2$, $CuInSe_2$/ZnS, ZnSe:Mn, ZnSe:Mn/ZnS, ZnSe:Cu, ZnSe:Cu/ZnS, ZnSe/ZnMnS/ZnS, CdSe:Ag, CdSe:Ag/ZnS, PbS, PbS/ZnS, PbSe, PbSe/CdSe, PbSe/CdSe/ZnSe, ZnSe/ZnMgS/ZnS, $ZnSeMn_x$/ZnS, $CdS/Cd_xZn_{(1-x)}S$, $CdSe/Cd_xZn_{(1-x)}S$, $CdSe_xTe_{(1-x)}/Cd_yZn_{(1-y)}S$, $AgInS_2$/ZnS, $CuInS_2$/ZnS, $AgInSe_2$/ZnS, and $CuInSe_2$/ZnS, where x and y range from 0 to 1.

6. The sensor of claim 1, wherein the quantum dot comprises at least one coating chosen from a phase transfer coating, a ligand exchange coating, a polymer coating and a silanization coating.

7. The sensor of claim 1, wherein the sensor is selective towards the HS⁻ anion compared to other thiols chosen from glutathione and cysteine.

8. The sensor of claim 1, wherein the sensor provides for a linear correlation of the integrated emission ratio of the QD:dye as a function of the HS⁻ concentration over a broader range of bisulfide analyte concentrations then the same QD donor and dye acceptor combination without the disulfide bridge.

* * * * *